(12) United States Patent
Davidson et al.

(10) Patent No.: US 11,154,533 B2
(45) Date of Patent: Oct. 26, 2021

(54) TOPICAL COMPOSITIONS AND METHODS FOR TREATING INFLAMMATORY SKIN DISEASES

(71) Applicant: Azora Therapeutics, Inc., Encino, CA (US)

(72) Inventors: Matthew Davidson, Encino, CA (US); Julie Saiki, Redwood City, CA (US); Johan Andreasson, Redwood City, CA (US)

(73) Assignee: Azora Therapeutics, Inc., Encino, CA (US)

( * ) Notice: Subject to any disclaimer, the term of this patent is extended or adjusted under 35 U.S.C. 154(b) by 0 days.

(21) Appl. No.: 17/194,146

(22) Filed: Mar. 5, 2021

(65) Prior Publication Data

US 2021/0186931 A1 Jun. 24, 2021

Related U.S. Application Data

(63) Continuation of application No. PCT/US2020/028581, filed on Apr. 16, 2020.

(60) Provisional application No. 62/924,611, filed on Oct. 22, 2019, provisional application No. 62/835,451, filed on Apr. 17, 2019.

(51) Int. Cl.
| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/404* | (2006.01) |
| *A61K 9/00* | (2006.01) |
| *A61K 9/06* | (2006.01) |
| *A61K 47/06* | (2006.01) |
| *A61K 47/44* | (2017.01) |

(52) U.S. Cl.
CPC .......... *A61K 31/404* (2013.01); *A61K 9/0014* (2013.01); *A61K 9/06* (2013.01); *A61K 47/06* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 5,981,586 | A * | 11/1999 | Pershadsingh | A61K 31/192 514/543 |
| 9,833,438 | B2 | 12/2017 | Andres et al. | |
| 2011/0207765 | A1 * | 8/2011 | Van Den Bussche | A61K 9/06 514/292 |
| 2012/0213868 | A1 | 8/2012 | Lin | |
| 2016/0114036 | A1 * | 4/2016 | Park | C07K 16/241 530/388.15 |
| 2016/0338973 | A1 | 11/2016 | Sonti et al. | |
| 2017/0304381 | A1 | 10/2017 | Chantalat et al. | |
| 2018/0169171 | A1 | 6/2018 | Bornstein et al. | |

FOREIGN PATENT DOCUMENTS

| | | |
|---|---|---|
| EP | 3093016 A1 | 12/2016 |
| WO | WO 2012/015914 A2 | 2/2012 |
| WO | WO 2016/168685 A1 | 10/2016 |
| WO | WO 2020/214855 A1 | 10/2020 |

OTHER PUBLICATIONS

"Benvitimod", Wikipedia, 2 pages, Online article downloaded from https://en.wikipedia.org/wiki/Benvitimod (2020).
Ensley et al., "Expression of naphthalene oxidation genes in *Escherichia coli* results in the biosynthesis of indigo", vol. 222, No. 4620, pp. 167-169 (1983).
Hubbard et al., "Indole and Tryptophan Metabolism: Endogenous and Dietary Routes to Ah Receptor Activation", Drug Metab. Dispos., vol. 43, pp. 1522-1535 (2015).
International Search Report from International Patent Application No. PCT/US2020/028581, dated Jun. 7, 2020, application now published as International Publication No. WO2020/214855 dated Oct. 22, 2020.
Jemec, "Hidradenitis Suppurativa", New England J. Med., vol. 366, No. 2, pp. 158-164 (2012).
Lin et al., "Comparison of Refined and Crude Indigo Naturalis Ointment in Treating Psoriasis: Randomized, Observer-Blind, Controlled, Intrapatient Trial", Arch. Dermatol., vol. 148, No. 3, pp. 397-400 (2012).
Lin et al., "Comparison of indirubin concentrations in indigo naturalis ointment for psoriasis treatment: a randomized, doubleblind, dosage-controlled trial", British J. Dermatol., vol. 178, pp. 124-131 (2018).
Noakes et al., "The Aryl Hydrocarbon Receptor: A Review of its Role in the Physiology and Pathology of the Integument and its Relationship to the Tryptophan Metabolism", Int. J. Tryptophan Res., vol. 8, pp. 7-18, (2015).
Mulero-Navarro and Fernandez-Salguero, "", Fronteirs in Cell Dev. Biol., vol. 4. Article 45, 14 pages (2016).
Saygin et al., Characteristics of inflammatory eye disease associated with hidradenitis suppurativa, Eur. J. Rhuematol., vol. 5, No. 3, pp. 165-168 (2018).

(Continued)

*Primary Examiner* — Layla Soroush
(74) *Attorney, Agent, or Firm* — McDermott Will & Emery LLP; Judy M. Mohr

(57) ABSTRACT

Compositions and methods for treating skin conditions, ailments or diseases, such as autoinflammatory skin diseases such as psoriasis, dermatitis, pyoderma gangrenosum, palmoplantar pustulosis, prurigo nodularis and/or hidradenitis suppurativa, are described. The compositions comprise an agent that modulates the aryl hydrocarbon receptor, in particular an agent that agonizes the receptor. In one embodiment, the agent is indigo or a derivative of indigo, such as indirubin.

18 Claims, 5 Drawing Sheets

(56) References Cited

OTHER PUBLICATIONS

Smith et al., "Development of a Topical Treatment for Psoriasis Targeting RORγ: From Bench to Skin", PLoS ONE, vol. 11, No. 2, 18 pages (2016).
Smith et al., "Tapinarof Is a Natural AhR Agonist that Resolves Skin Inflammation in Mice and Humans", J. Inv. Dermatol., vol. 137, pp. 2110-2119 (2017).
Zouboulis et al., "Development and validation of the International Hidradenitis Suppurativa Severity Score System (IHS4), a novel dynamic scoring system to assess HS severity", Br.J. Dermatol., vol. 177, No. 5, pp. 1401-1409 (2017).
Holgate et al., "Efficacy and safety of etanercept in moderate-to-severe asthma: a randomized controlled trial", Eur.Respir. J., vol. 37, pp. 1352-1359 (2011).
Lee et al., "A prospective clinical trial of open label etanercept for the treatment of hidradenitis suppurativa", J. Am. Acad. Dermatol., vol. 60, No. 4, pp. 565-573 (2009).
Strober et al., "Etanercept does not effectively treat moderate to severe alopecia areata: An open-label study", J. Am. Acad. Dermatol., vol. 52, No. 6, pp. 1082-1084 (2005).
U.S. National Library of Medicine, "Use of Etanercept in the Treatment of Moderate to Severe Lichen Planus", ClinicalTrials.gov, 25 pages (2006), Online article downloaded from: https://www.clinicaltrials.gov/ct2/show/results/NCT00285779?intr=enbrel&draw=2&view=results.

\* cited by examiner

TOPICAL COMPOSITIONS AND METHODS FOR TREATING INFLAMMATORY SKIN DISEASES

CROSS-REFERENCE TO RELATED APPLICATIONS

This application is a continuation of PCT Application No. PCT/US20/28581, filed Apr. 16, 2020, which claims the benefit of U.S. Provisional Application No. 62/924,611, filed Oct. 22, 2019, and of U.S. Provisional Application No. 62/835,451, filed Apr. 17, 2019, each of which is incorporated by reference herein in its entirety.

TECHNICAL FIELD

The subject matter described herein relates to compositions and methods for treating subjects with inflammatory skin disease.

BACKGROUND

A number of inflammatory diseases profoundly impact the life of patients and have manifestations in the skin and/or mucosa. Many of these diseases are autoinflammatory targeting self-proteins or the commensal microbiota. These diseases include but are not limited to psoriasis (Ps), atopic dermatitis (AD), contact dermatitis, hidradenitis suppurativa (HS), pyoderma gangrenosum (PG), Sweet's syndrome, mutations in the PSTPIP-1 gene (PAPA syndrome, PAPSH syndrome and PASH syndrome), Bechet's disease, bullous pemphigold, mucous membrane pemphigold, pemphis vulgaris, cutaneous Crohn's disease, Sjögren syndrome, systemic lupus erythematosus, prurigo nodularis (PN), pityriasis lichenoides chronica, palmoplantar pustulosis (PPP), pyoderma gangrenosum (PG) and erythoderma. In many cases, the pathophysiologies of the diseases are not well understood, limiting a rational treatment approach. Interestingly, many of these diseases have been associated with rheumatoid arthritis and inflammatory bowel diseases such as ulcerative colitis or Crohn's disease and may share an underlying pathophysiology characterized by a Th17 type response and infiltrating lymphocytes and neutrophils.

For example, HS is a chronic follicular occlusive disease involving the follicular portion of folliculopilosebaceous units of apocrine gland-bearing skin. Patients can present with recurrent nodules, sinus tracts formation, abscesses, and/or scarring. The disease can manifest anywhere there are apocrine glands or hair follicles including the underarm, groin, buttocks and under the breasts. Symptoms may include pus-filled papules, cysts or nodules which may be painful and often emit an off-putting smell. HS is a chronic disease without a cure that has a severely negative impact on quality of life.

Aryl hydrocarbon receptor (AhR) agonists have been used clinically to treat auto-inflammatory diseases including ulcerative colitis, multiple sclerosis, atopic dermatitis and psoriasis. AhR agonists include, for example, compounds such as indigo and indigo derivatives including, indirubin, meisoindigo, natura-alpha (glycosylated isoindigotin); clinical-stage drugs such as tapinarof, linomide (roquinimex) and laquinimod; regulatory approved drugs such as itraconazole, ketoconazole, omeprazole, and leflunomide; naturally occurring compounds such as FICZ (5,11-dihydro-indolo[3,2-b]carbazole-6-carboxaldehyde, 6-Formylindolo[3,2-b] carbazole) and indole derivatives; and polyaromatic hydrocarbons such as 2,3,7,8-tetrachlorodibenzo-p-dioxin (TCDD), coal tar, refined coal tar, and components of tobacco combustion. With the exception of psoriasis and atopic dermatitis, AhR agonists have not been used clinically to treat auto-inflammatory diseases that manifest in the skin.

BRIEF SUMMARY

The following aspects and embodiments thereof described and illustrated below are meant to be exemplary and illustrative, not limiting in scope.

In one aspect, a topical composition is provided that comprises an oleaginous compound, a solvent, and between about 0.001-0.3 weight percent indirubin.

In some embodiments, the composition optionally comprises a wax, and in one embodiment the wax is a non-naturally occurring wax. The wax, when present, is, in some embodiments, present in the composition at between about 12-60 wt %. In some embodiments, the wax is a solid at room temperature (about 25° C.). Exemplary waxes include beeswax, paraffin wax, cetyl alcohol, and lanolin.

In an embodiment, the oleaginous compound is a liquid at room temperature (about 25° C.). In an embodiment, the oleaginous compound is present in the composition at between about 8-90 wt %, 10-80 wt %, 10-65 wt %, 15-80 wt %, or 20-65 wt %. In some embodiments, the oleaginous compound is a synthetic compound with at least about 8, 9, 10, 11, 12, 13, 14, 15, 16, 17, 18 or 20 carbon atoms. In embodiments, the oleaginous compound is oleic acid, diethyl sebacate. In other embodiments, the oleaginous compound is a plant based oil, such as olive oil or castor oil. In other embodiments, the oleaginous compound is a petroleum based oil, such as mineral oil.

In one embodiment, the solvent is an aprotic solvent. In another embodiment, the solvent has a molecular weight of less than about 100 g/mol. In some embodiments, the solvent is present in the composition at between about 2.5-35 wt % or 5-35 wt %. In other embodiments, the solvent is non-oleaginous.

In another embodiment, the solvent is selected from the group consisting of dimethylsulfoxide, n-methyl-2-pyrrolidone, diethylene glycol monoethyl ether, isopropyl myristate, glycerol, and/or propylene glycol. In another embodiment, the solvent is an aprotic solvent selected from the group consisting of dimethylsulfoxide, n-methyl-2-pyrrolidone, diethylene glycol monoethyl ether, and isopropyl myristate. In another embodiment, the solvent is selected from glycerol and propylene glycol.

In still other embodiments, the solvent is two or more solvents. In some embodiments, the two or more solvents are or include propylene glycol and dimethylsulfoxide.

In other embodiments, the composition further comprises a surfactant, a thickening agent, or both.

In some embodiments, the indirubin is synthetic indirubin. In some embodiments, the synthetic indirubin is essentially free of impurities, such as indigo, tryptanthrin and qingdianone. In one embodiment, the synthetic indirubin comprises less than about 0.1 wt % indigo, tryptanthrin and qingdianone.

In other embodiments, the composition, when topically applied to human skin at 10 mg/cm$^2$ in vitro or in vivo, provides one or more of (i) a non-therapeutic systemic blood level of indirubin, (ii) more than about 14.7 ng per cm$^2$ of indirubin into the epidermis when applied to the skin for 24 hours (iii) more than about 16.9 ng per cm$^2$ of indirubin into the dermis when applied to the skin for 24 hours; and (iv)

upregulation of CYP1A1 in the skin more than 100-fold relative to the same composition lacking synthetic indirubin.

In another aspect, a topical composition is provided that comprises synthetic indirubin in an amount of greater than about 0.01 wt % and equal to or less than 0.2 wt %, and a pharmaceutically acceptable carrier that forms an ointment wherein the indirubin is essentially completely dissolved in the ointment. In an embodiment, the synthetic indirubin comprises less than 0.1 wt % indigo, tryptanthrin and qingdianone, and in other embodiments the composition, topically applied to human skin at 10 mg/cm$^2$ in vitro or in vivo, provides one or more of (i) a non-therapeutic systemic blood level of indirubin, (ii) more than about 14.7 ng per cm$^2$ of indirubin into the epidermis when applied to the skin for 24 hours (iii) more than about 16.9 ng per cm$^2$ of indirubin into the dermis when applied to the skin for 24 hours; and (iv) upregulation of CYP1A1 in the skin more than 100-fold relative to the same composition lacking synthetic indirubin.

In another aspect, a method for alleviating symptoms associated with an inflammatory skin disease is provided. The method comprises administering to a subject a therapeutically effective amount of a composition comprising an AhR agonist.

In another aspect, a method for treating an inflammatory skin disease in a subject previously treated for the inflammatory skin disease by administration of a composition comprising an active agent that is not an AhR agonist is provided. The method comprises administering to a subject a therapeutically effective amount of a composition comprising an AhR agonist, thereby treating the inflammatory skin disease in the subject.

In yet another aspect, a method for preventing recurrence of symptoms associated with an inflammatory skin disease or for reducing frequency of an inflammatory skin disease or for reducing frequency of new lesions, abscesses or nodules associated with an inflammatory skin disease in a subject diagnosed with an inflammatory skin disease is provided. The method comprises administering to a subject a therapeutically effective amount of a composition comprising an AhR agonist, thereby preventing recurrence of symptoms associated with the inflammatory skin disease or reducing frequency the inflammatory skin disease in the subject.

In one embodiment, the inflammatory skin disease is pyoderma gangrenosum.

In another embodiment, the inflammatory skin disease is psoriasis.

In yet another embodiment, the inflammatory skin disease is atopic dermatitis.

In still another embodiment, the inflammatory skin disease is contact dermatitis.

In another embodiment, the inflammatory skin disease is palmoplantar pustulosis

In another embodiment, the inflammatory skin disease is prurigo nodularis.

In another embodiment, the inflammatory skin disease is hidradenitis suppurativa.

In other aspects, methods for treating hidradenitis suppurativa (HS), pyoderma gangrenosum (PG), psoriasis (Ps), atopic dermatitis (AD), palmoplantar pustulosis (PPP), and/or prurigo nodularis (PN) are provided. The methods comprise administering to a subject a therapeutically effective amount of a composition comprising an aryl hydrocarbon receptor agonist or modulating agent, thereby treating or preventing HS, PG, psoriasis and/or atopic dermatitis in the subject.

In another aspect, a method for alleviating symptoms associated with HS, PG, Ps, AD, PPP and/or PN comprises administering to a subject a therapeutically effective amount of a composition comprising an aryl hydrocarbon receptor agonist or modulating agent, thereby alleviating symptoms associated with HS, PG, Ps, AD, PPP and/or PN in the subject.

In yet another aspect, a method for treating HS, PG, Ps, AD, PPP and/or PN in a subject previously treated for HS, PG, Ps, AD, PPP and/or PN by administration of an active agent other than an aryl hydrocarbon receptor agonist, such as, for example, an antibiotic, a retinoid, a Janus kinase inhibitor, a PDE-4 inhibitor, a complement inhibitor, an anti-TNF-alpha antibody, an anti-IL-17 antibody, an anti-IL-23 antibody, anti-androgens and/or a steroid. The method comprises administering to the subject a therapeutically effective amount of a composition comprising an aryl hydrocarbon receptor agonist or modulating agent, thereby treating HS, PG, Ps, AD, PPP and/or PN in the refractory subject.

In still another aspect, a method for preventing recurrence of symptoms associated with HS, PG, Ps, AD, PPP and/or PN or for reducing frequency of HS, PG, Ps, AD, PPP and/or PN in a subject diagnosed with HS, PG, Ps, AD, PPP and/or PN is provided. The methods comprise administering to the subject a therapeutically effective amount of a composition comprising an aryl hydrocarbon receptor agonist or modulating agent, thereby preventing recurrence of symptoms or reducing frequency of HS, PG, Ps, AD, PPP and/or PN in the subject.

In an embodiment suitable to any of the aspects mentioned herein, the composition comprises as the aryl hydrocarbon receptor agonist or modulating agent tapinarof, indigo and/or an indigo derivative. In one embodiment, the aryl hydrocarbon receptor agonist is a prodrug of indigo or a prodrug of an indigo derivative.

In one embodiment suitable to any of the aspects mentioned herein, the composition is *Indigo naturalis*. In another embodiment suitable to any of the aspects mentioned herein, the composition is not *Indigo naturalis*, the composition does not comprise as the AhR receptor agonist indigo, and/or the composition does not comprise as the AhR receptor agonist natural indirubin. In another embodiment suitable to any of the aspects mentioned herein, the composition does not comprise as the AhR receptor agonist any of the ingredients of *Indigo naturalis*. Rather, the compositions described herein, in one embodiment, comprise synthetic indirubin, in base or salt form.

In one embodiment suitable to any of the aspects mentioned herein, the composition is topically administered to a skin region on the subject affected by the inflammatory skin disease.

In another embodiment suitable to any of the aspects mentioned herein, the composition comprises indigo and/or an indigo derivative. In one embodiment, the indigo and/or indigo derivative is one of indigo, indirubin, and/or isatin. In one embodiment, the composition comprising one of indigo, indirubin, and/or isatin is not *Indigo naturalis*. In another embodiment, the composition comprising one of indigo, indirubin, and/or isatin is a composition comprising one or more of synthetically produced indigo, indirubin, and/or isatin. In another embodiment, the composition comprising one of indigo, indirubin, and/or isatin is a composition comprising one or more of synthetically produced prodrugs of indigo, indirubin, and/or isatin.

In an embodiment, the methods comprise topically administering the composition to a region on the subject affected by the autoimmune disease or disorder (e.g., HS, PG, Ps, AD, PPP and/or PN). In one embodiment, the region affected by disease or disorder is non-intact skin. In another embodiment, the region affected by the disease or disorder is intact skin.

In any of the above embodiments, the disease being treated is chosen from any autoimmune or autoinflammatory disease including but not limited to psoriasis, pyoderma gangrenosum, atopic dermatitis, contact dermatitis, palmar plantar pustulosis, and/or prurigo nodularis.

In another embodiment, the methods comprise administering the composition at least about once daily, at least about twice daily, at least three times daily. In one embodiment, the composition is administered for a period of at least 4 weeks, 6 weeks, 8 weeks, 10 weeks or 12 weeks.

In still another embodiment, the composition is formulated as a gel, a cream, a lotion, a suspension, a semisolid, a foam, an oil, a lacquer, a form-filming solution, or an ointment.

In still another embodiment the topical composition may result sub therapeutic blood or plasma levels, below the $EC_{50}$ for the AhR. In particular for indirubin, the topical composition may result in blood levels below about 0.1 ng/mL, below about 0.5 ng/mL, below about 1 ng/mL, below about 2 ng/mL, below about 5 ng/mL, below about 10 ng/mL or below about 20 ng/mL. In another embodiment, the blood level resulting from the topical composition is between any two of the values recited in the previous sentence.

In one embodiment, the composition is an extract of *Baphicacanthus cusia* (Nees) Bremek of the Acanthacaea family.

In yet another embodiment, the extract is from stems and leaves of *Baphicacanthus cusia* (Nees) Bremek.

In still another embodiment, the composition is an extract of one or more of the plants *Indigofera tinctoria, Indigofera suffruticosa, Polygonum tinctorium, Isatis indigotica*.

In yet another embodiment, the composition comprises a compound selected from indigo, indirubin, and isatin, and a pharmaceutically acceptable carrier, wherein the composition is not *Indigo naturalis*. In another embodiment, the composition comprises at least two compounds selected from indigo, indirubin, and isatin, and a pharmaceutically acceptable carrier, wherein the composition is not *Indigo naturalis*.

In an embodiment, the weight percent of the at least two compounds relative to the weight percent of the compounds in the composition is selected from the following:
(i) between about 55-95% indirubin, 5-45% indigo, and 0-40% isatin;
(ii) between about 40-80% indirubin, 20-60% indigo, and 0-40% isatin;
(iii) between about 20-60% indirubin, 40-80% indigo, and 0-40% isatin;
(iv) between about 0-40% indirubin, 55-95% indigo, and 5-45% isatin;
(v) between about 0-40% indirubin, 40-80% indigo, and 20-60% isatin;
(vi) between about 0-40% indirubin, 20-60% indigo, and 40-80% isatin;
(vii) between about 5-45% indirubin, 0-40% indigo, and 55-95% isatin;
(viii) between about 20-60% indirubin, 0-40% indigo, and 40-80% isatin; and
(ix) between about 40-80% indirubin, 0-40% indigo, and 20-60% isatin.

In one embodiment, the compound is/are synthetically produced. In another embodiment, the compound is/are isolated from an extract or enriched in an extract by suitable processing.

In another embodiment, the subject treated in accord with the methods is selected from the group consisting of subjects diagnosed with Hurley stage I HS, Hurley stage II HS and Hurley stage III HS.

In another aspect, a topical composition is provided. The composition comprises one, two or more compounds selected from indigo, indirubin, and isatin, and a pharmaceutically acceptable carrier. In one embodiment, the composition is not *Indigo naturalis*. The composition provides a therapeutic effect that is substantially the same as provided by a composition of *Indigo naturalis*, in one embodiment.

In another aspect, a composition comprises a compound selected from indigo, indirubin, isatin and combinations thereof, and a pharmaceutically acceptable carrier, wherein the compound is synthetically produced, and wherein the composition provides a therapeutic effect with respect to treating HS that is substantially the same as provided by a composition of *Indigo naturalis*.

In one embodiment, the composition provides a synergistic effect with respect to treating the autoimmune disease or disorder as compared to the effect provided by a composition of *Indigo naturalis*.

In another embodiment, the composition provides a reduction in observed side effects compared to the side effects observed following administration of *Indigo naturalis*. In one embodiment, the composition provides a reduction in one or more of the following side effects of *Indigo naturalis*: skin irritation, skin pigmentation, folliculitis, dermatitis, erythema, pruritus, changes in liver enzymes, development of pulmonary or vasculature adverse events such as pulmonary arterial hypertension or skin discoloration or staining.

In yet another embodiment, the composition provides a synergistic effect with respect to treating the autoimmune disease or disorder as compared to the effect provided by a composition of the carrier and indigo, indirubin, or isatin individually.

In one embodiment, at least one of the at least two compounds is present in the composition in an amount at least 10% greater than in *Indigo naturalis*.

In another embodiment, at least one of the at least two compounds is present in the composition in an amount at least 10% less than in *Indigo naturalis*.

In one embodiment, the at least two compounds are indirubin and indigo.

In another embodiment, indirubin and indigo are present in the composition in a ratio of indirubin to indigo from about 1:30 to 30:1.

In one embodiment, the at least two compounds are indirubin and isatin.

In another embodiment, the indirubin and isatin are present in the composition in a ratio of indirubin to isatin from about 1:30 to 30:1.

In one embodiment, the at least two compounds are indigo and isatin.

In another embodiment, the indigo and isatin are present in the composition in a ratio of indigo to isatin from about 1:30 to 30:1.

In another aspect, a topical composition comprised of indirubin, and a pharmaceutically acceptable carrier is provided, wherein the indirubin is synthetic indirubin, and wherein the composition is essentially free of indigo and/or isatin. In one embodiment, the composition comprises less than about 3% indigo and/or isatin. In one embodiment, the composition comprises indirubin and comprises less than about 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% indigo and/or isatin.

In one embodiment, the composition with synthetic indirubin provides a therapeutic effect that is substantially the same as provided by a topically applied composition of *Indigo naturalis*.

In another embodiment, the composition is suitable for localized delivery.

In an embodiment, the localized delivery is topical delivery to intact or disrupted skin.

In an embodiment, the topical delivery is via a dermal patch or microneedle patch.

In an embodiment, the topical delivery is via a dressing.

In one embodiment, the composition when topically applied yields a non-therapeutic blood level of the synthetic indirubin, indigo and/or isatin.

In another embodiment, the composition yields no measurable systemic blood level of the synthetic indirubin, indigo and/or isatin for example, 24 hours or 48 hours after topical administration in accord with the methods of treatment described herein for treatment of a condition described herein. In another embodiment, the composition yields no physiologically relevant systemic blood level of the synthetic indirubin, indigo and/or isatin for example, 24 hours or 48 hours after topical administration in accord with the methods of treatment described herein for treatment of a condition described herein.

In one embodiment, the carrier is suitable for topical administration.

In addition to the exemplary aspects and embodiments described above, further aspects and embodiments will become apparent by study of the following description.

Additional embodiments of the present methods and compositions, and the like, will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any other embodiment.

DETAILED DESCRIPTION

I. Definitions

Figure 1A:
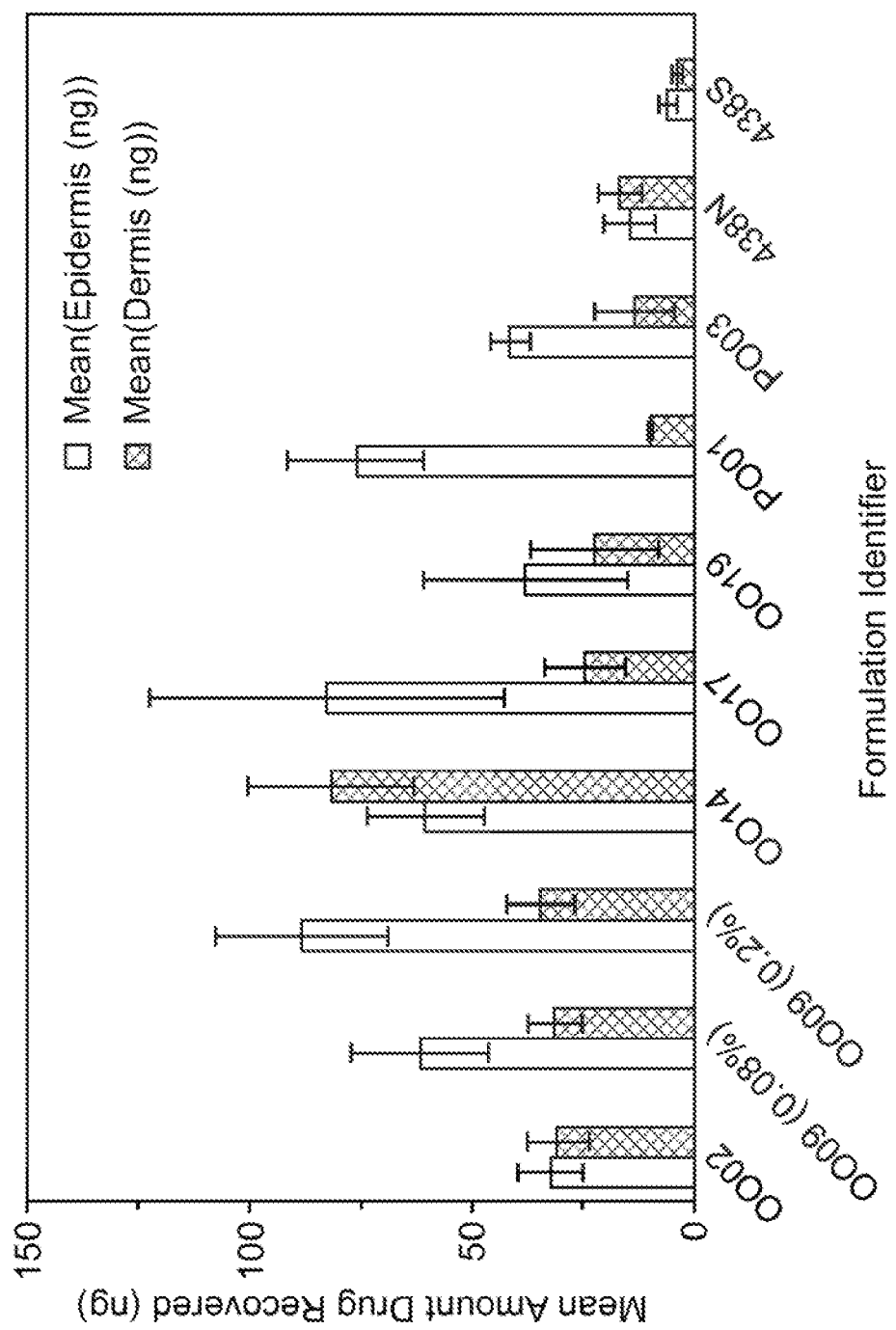
FIG. 1A is a bar graph showing the mean amount of drug recovered, in ng, in the epidermis (open bars) and dermis (bars with cross-hatch fill) for ten formulations prepared and tested as described herein.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

All percentages, parts and ratios are based upon the total weight of the topical compositions and all measurements made are at about 25° C., unless otherwise specified.

The term "indigo," as used herein, generally refers to a compound having the formula below identified as "indigo."

An "indigo derivative" refers to derivatives of indigo such as those exemplified by the compounds identified below as leuco-indigo, leuco-indirubin, indirubin, meisoindigo, and/or isatin (an oxidized version of half of the indigo molecule):

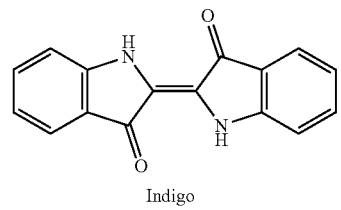

Indigo

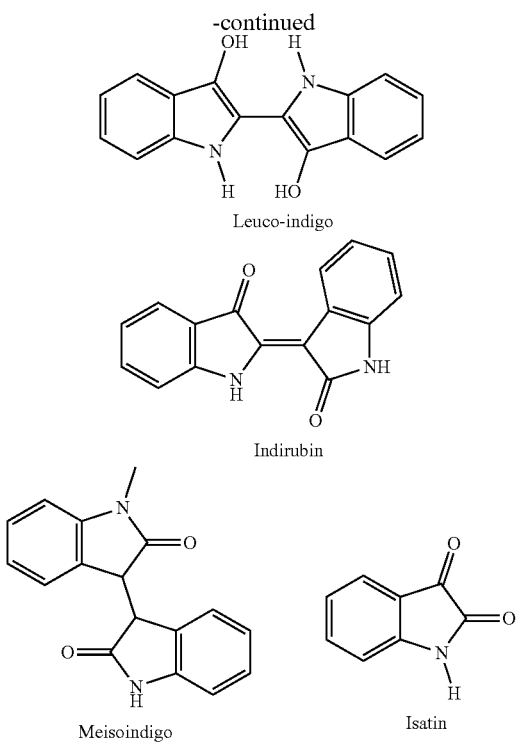

Additional non-limiting examples of indigo derivatives include thioindigo, indigo carmine, indirubin-3′-monoxime, indirubin-5-sulphonic acid or 5-chloro-indirubin, bromoindirubin-3-oxime, 5-halogenoindirubin, N-ethyl-indirubin, N-methylisoindigo, the compounds set forth in U.S. Patent Application Publication No. 2017/0304381, which is incorporated by reference herein, the compounds set forth in Hubbard, T. D. et al., *Drug Metabolism and Disposition*, 43:1522-1535 (2015), which is incorporated by reference herein. The term "indigo derivative" excludes prodrugs of indigo and indigo derivatives unless express reference is made to "prodrug of indigo" or "prodrug of an indigo derivative."

"*Indigo naturalis*" or IN, refers to a plant extract that contains indigo and other indigo derivatives. This extract can be crude or highly purified to enrich for indigo and/or an indigo derivative. The plant extract can be from the species *Indigofera tinctoria, Indigofera suffruticosa, Polygonum tinctorium, Isatis indigotica, Baphicacanthus cusia* or other plants or yeast or bacteria that contain indigo.

The terms "inhibiting" or "reducing" are used in reference to methods to inhibit or to reduce a clinical symptom of a disorder in a population with the disorder as compared to an untreated, control population of subjects with the disorder.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

Pharmaceutically acceptable salt" denotes a salt form of a drug or active ingredient, or other ingredient having at least one group suitable for salt formation that causes no significant adverse toxicological effects to the patient. Reference to an AhR agonist compound, such as indirubin, is meant to encompass its pharmaceutically acceptable salts, as well as solvates and hydrates thereof. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate and phosphate. Suitable pharmaceutically acceptable salt forms and methods for identifying such salts are found in, e.g., Handbook of Pharmaceutical Salts: Properties, Selection and Use, Weinheim/Zürich:Wiley-VCH/VHCA, 2002; P. H. Stahl and C. G. Wermuth, Eds.

"Substantially" or "essentially" means nearly totally or completely, for instance, 95% or greater, of a given quantity.

The term "treating" is used herein, for instance, in reference to methods of treating an inflammatory skin disorder, and generally includes the administration of a compound or composition which reduces the frequency of, or delays the onset of, symptoms of the medical condition (e.g., HS) in a subject relative to a subject not receiving the compound or composition. This can include reversing, reducing, alleviating, or arresting the symptoms, clinical signs, and/or underlying pathology of a condition in a manner to improve or stabilize a subject's condition.

The term "topical composition" refers to a material that comprises pharmaceutically acceptable ingredients, including an active indigo agent, and is intended for administration to an animal or human subject and is applied to the surface of the skin, in contrast to materials that are taken orally or via intravenous (subdermal) injection. A topical composition is generally intended to have its intended effect at the site of application and does not result in significant concentrations of drug in the bloodstream or other tissues (as is the case with, for example, transdermal compositions). Topical compositions as provided herein are typically administered for the purpose of alleviation of symptoms associated with a dermatological disease or condition, treatment of a dermatological disease or condition, or prevention of a dermatological disease or condition.

The term "substantially" or "essentially" in reference to a certain feature or entity means to a significant degree or nearly completely (i.e. to a degree of 85% or greater) in reference to the feature or entity.

The compositions of the present disclosure can comprise, consist essentially of, or consist of, the components disclosed.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

II. Methods of Treatment

Methods for treating an autoinflammatory skin disease, for alleviating symptoms associated with an autoinflammatory skin disease, for preventing recurrence of symptoms associated with an autoinflammatory skin disease and/or for reducing frequency of an autoinflammatory skin disease are provided. The methods comprise administering to a subject a therapeutically effective amount of a composition comprising an aryl hydrocarbon receptor agonist or modulating agent and a pharmaceutically acceptable carrier. The methods are based, in part, on a finding that the aryl hydrocarbon receptor (AhR) system can modulate the immune response, and that agonists of AhR are useful therapeutic agents for treating autoimmune diseases. Described below are compositions for use in the methods, approaches for administering the compositions, and other details in connection with the methods.

A. Compositions

Compositions for use in the methods described herein comprise an AhR agonist or modulating agent.

Examples of AhR agonists include tapinarof (3,5-dihydroxy-4-isopropyl-trans-stilbene; Smith, et al., *J. Invest. Dermatol.*, 137(1):2110-2119 (2017)); 3-methyl cholanthrene, dioxin, 3',4'-dimethoxy-a-naphthoflavone (DiMNF), 3,3'-Diindolylmethane (DEVI), resveratrol, curcumin, indigo and indigo derivatives. Other exemplary AhR agonists are described in Hubbard, T. D. et al., *Drug Metabolism and Disposition*, 43:1522-1535 (2015) and in WO 2012/015914, which are incorporated by reference herein. Compounds that agonize the AhR can be identified, for example, as described in WO2016/168685.

In some cases AhR agonists may include approved drugs, salts of approved drugs, or prodrugs that decompose or are metabolized to approved drugs with AhR agonist activity and include itraconazole, ketoconazole, omeprazole, and leflunomide.

The composition, in one embodiment, comprises tapinarof, salts or prodrugs thereof, and an acceptable carrier. Exemplary carriers are described, infra.

The composition, in one embodiment, comprises indigo and/or an indigo derivative and an acceptable carrier. In one embodiment, the composition is *Indigo naturalis*. In other embodiments, the composition comprising indigo and/or an indigo derivative is not *Indigo naturalis*, yet is a composition comprising one or more of indigo, indirubin, and/or isatin. For example, the composition can be an extract that is enriched in one or more of indigo or an indigo derivative, such as indirubin and/or isatin. Alternatively, the composition can be a formulation comprised of one or more of a synthetically manufactured indigo and/or an indigo derivative. Exemplary compositions of indigo and indigo derivatives, as illustrative of compositions with an AhR agonist, are now described.

A composition comprised of *Indigo naturalis* or an extract thereof is contemplated for use in the methods. *Indigo naturalis* (also called Qing Dai) is prepared from dried and fermented materials from the plants *Indigofera tinctoria, Indigofera suffruticosa, Polygonum tinctorium*, and/or *Isatis indigotica*. One exemplary *Indigo naturalis* composition is an extract of *Baphicacanthus cusia* (Nees) Bremek of the Acanthacaea family highly enriched in indirubin. In some cases, the extract is from stems and leaves of *Baphicacanthus cusia* (Nees) Bremek.

The *Indigo naturalis* composition is applied topically for use in treating HS and can be formulated with a carrier to ease topical application and/or enhance penetration, if desired. Exemplary carriers are described below.

In another embodiment, a composition that is not *Indigo naturalis* or an extract of *Indigo naturalis* and that is comprised of indigo and/or an indigo derivative is contemplated. In these compositions, indigo and/or the indigo derivative may be synthetically produced, extracted and/or isolated from plants, or made via fermentation or bioreactor. Chemical synthesis and biosynthesis of indigo and/or indigo derivatives is described, for example, in Ensley et al., *Science*, 167 (1983). Processing of plants to enrich the extract in one or more of indigo and/or an indigo derivative is another approach to production of a composition, that is not *Indigo naturalis*, and that is comprised of indigo and/or an indigo derivative.

In a first embodiment, a composition comprises a compound selected from indigo, indirubin, isatin, and combinations thereof, and a pharmaceutically acceptable carrier, wherein the composition provides a therapeutic effect with respect to treating HS that is substantially the same as provided by a composition of *Indigo naturalis*. Alternatively, the composition may provide a synergistic effect with respect to treating HS as compared to the effect provided by a composition of *Indigo naturalis*. Alternatively, the composition may provide a reduction in observed side effects and/or increased efficacy compared to the side effects observed following administration of *Indigo naturalis*. Examples of side effects observed upon topical application of *Indigo naturalis* or extracts of *Indigo naturalis* can be, for example, skin irritation, skin pigmentation changes, erythema, pruritus, folliculitis, dermatitis, and/or skin discoloration or staining. Alternatively, the composition provides a synergistic effect with respect to treating HS as compared to the effect provided by a composition of the carrier and indigo, indirubin, or isatin individually.

In one embodiment, the active agent compound or compounds in the composition, e.g., indigo, indirubin, and/or isatin, is/are synthetically produced or synthesized compounds. In another embodiment, the active agent compound or compounds in the composition, e.g., indigo, indirubin, and/or isatin, is/are isolated from a plant extract and/or resulting from processing of a plant extract to obtain a refined extract that consists of the one or more compound or compounds. That is, the processing technique removes from the extract compounds with therapeutic activity other than the specifically desired compounds. The therapeutically active compound, whether synthetically produced or obtained from a processing technique of a plant extract, is combined with a pharmaceutically acceptable carrier to provide a composition.

Compositions comprising a single therapeutic compound, in some embodiments, comprise between about 0.001-15 wt %, 0.001-10 wt %, 0.001-5 wt %, 0.001-3 wt %, 0.001-0.1 wt %, 0.001-0.3 wt %, 0.001-0.2 wt %, 0.01-15 wt %, 0.01-10 wt %, 0.01-5 wt %, 0.05-15 wt %, 0.05-10 wt %, 0.05-5 wt %, 0.1-15 wt %, 0.1-10 wt %, 0.1-5 wt %, 0.2-15 wt %, 0.2-10 wt %, 0.2-5 wt %, 0.3-15 wt %, 0.3-10 wt %, 0.3-5 wt %, 0.4-15 wt %, 0.4-10 wt %, 0.4-5 wt %, 0.5-15 wt %, 0.5-10 wt %, 0.5-5 wt %, 0.6-15 wt %, 0.6-10 wt %, 0.6-5 wt %, 0.7-15 wt %, 0.7-10 wt %, 0.7-5 wt %, 0.8-15 wt %, 0.8-10 wt %, 0.8-5 wt %, 0.9-15 wt %, 0.9-10 wt %, 0.9-5 wt %, 1-15 wt %, 1-10 wt %, or 1-5 wt % of the single therapeutic compound based on the total weight of the composition. The therapeutic compound, can be indigo, an indigo derivative, or any other AhR agonist. In one embodiment, the compound is a synthetic compound and is not an extract from a plant or fermented botanical product.

In embodiments where the composition comprises at least two compounds selected from indigo, indirubin, and/or isatin the compounds are present, in some embodiments, in one of the following weight percentages based on the weight of the active agent (therapeutic) compounds in the composition (e.g., not based on total weight of the composition):

(i) between about 55-95% indirubin, 5-45% indigo, and 0-40% isatin;

(ii) between about 40-80% indirubin, 20-60% indigo, and 0-40% isatin;

(iii) between about 20-60% indirubin, 40-80% indigo, and 0-40% isatin;

(iv) between about 0-40% indirubin, 55-95% indigo, and 5-45% isatin;

(v) between about 0-40% indirubin, 40-80% indigo, and 20-60% isatin;

(vi) between about 0-40% indirubin, 20-60% indigo, and 40-80% isatin;

(vii) between about 5-45% indirubin, 0-40% indigo, and 55-95% isatin;

(viii) between about 20-60% indirubin, 0-40% indigo, and 40-80% isatin; or (ix) between about 40-80% indirubin, 0-40% indigo, and 20-60% isatin.

In some compositions comprised of indigo, indirubin, and/or isatin at least one of the compounds is present in the composition in an amount at least 10%, 15%, 20%, or 25% greater than in *Indigo naturalis*. In some compositions comprised of indigo, indirubin, and/or isatin at least one of the compounds is present in the composition at least one of the compounds is present in the composition in an amount at least 10%, 15%, 20%, or 25% less than in *Indigo naturalis*.

In one embodiment, the active agent in the compositions comprises, consists essentially of, or consists of indirubin and indigo; or indirubin and isatin; or indigo and isatin. When indirubin and indigo are present in the composition, they may be in a ratio of indirubin to indigo from about 1:30 to 30:1, 1:25 to 25:1, 1:20 to 20:1, 1:15 to 15:1, 1:10 to 10:1. When indirubin and isatin are present in the composition, they may be in a ratio of indirubin to isatin from about 1:30 to 30:1, 1:25 to 25:1, 1:20 to 20:1, 1:15 to 15:1, 1:10 to 10:1. When indigo and isatin are present in the composition, they may be in a ratio of indigo to isatin from about 1:30 to 30:1, 1:25 to 25:1, 1:20 to 20:1, 1:15 to 15:1, 1:10 to 10:1. Alternatively, the various combinations of active agents can be in a ratio of the first active agent to the second active agent from about from about 10:1 to 50:1, 15:1 to 50:1, 20:1 to 50:1, 25:1 to 50:1, 15:1 to 45:1, 20:1 to 45:1, 25:1 to 45:1, 30:1 to 45:1, 20:1 to 30:1, 20:1 to 35:1, 20:1 to 40:1, or 30:1 to 35:1. In another embodiment, the ratio of first active agent to the second active agent is about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, or 60:1.

In another embodiment, the composition comprises at least two compounds selected from indigo, indirubin, and isatin, and a pharmaceutically acceptable carrier, wherein the composition is not *Indigo naturalis*.

In embodiments, the weight percent of the first active agent (e.g, any AhR agonist), based on the total weight of the active agents in the composition, is between about 25-99 wt %, 25-98 wt %, 25-96 wt %, 25-95 wt %, 25-90 wt %, 25-85 wt %, 25-75 wt %, 25-70 wt %, 25-65 wt %, 25-60 wt %, 25-55 wt %, 25-50 wt %, 25-45 wt %, 25-40 wt %, or 25-35 wt %. In other embodiments, the weight percent of the second active agent (e.g., any AhR agonist different from the first AhR agonist), based on the total weight of the active agents in the composition, is between about 25-99 wt %, 25-98 wt %, 25-96 wt %, 25-95 wt %, 25-90 wt %, 25-85 wt %, 25-75 wt %, 25-70 wt %, 25-65 wt %, 25-60 wt %, 25-55 wt %, 25-50 wt %, 25-45 wt %, 25-40 wt %, or 25-35 wt %.

In any of the compositions described herein, indigo and indigo derivatives may be substituted with boron, $H^3$ or radioactive moieties. In any of the compositions described herein, indigo and/or indigo derivatives may be a pharmaceutically acceptable salt form.

In another embodiment, the AhR agonist compound is a prodrug of indigo or of an indigo derivative that decomposes or is metabolized into indigo and/or an indigo derivative or other AhR agonist. Examples of such prodrugs include indican, indoxyl, leuco-indigo, and the like. In one embodiment, the composition comprises indigo, an indigo derivative, a prodrug of indigo, a prodrug of an indigo derivative, and/or a combination of any of the foregoing. In another embodiment, the composition comprises indigo, an indigo derivative, a prodrug of indigo, and/or a combination thereof, exclusive of prodrugs of an indigo derivative. In another embodiment, the composition comprises an indigo derivative, a prodrug of indigo, a prodrug of an indigo derivative, and/or a combination thereof, exclusive of a prodrug of the indigo derivative indirubin.

In any of the compositions described herein, the AhR agonist compound can be in the form of a solid. This solid may be highly crystalline or bound to inorganic and organic material that has crystalized out of solution or been evaporated down into a solid. This material may be processed into a powder. The powder may have a uniform or widely distributed average particle size. The particle size may be on the nanometer scale, the micrometer scale or larger. Powders of uniform particle sizes may have different solubility or bioavailability based on their crystalline structure or lack thereof, surface area, co-crystals or isoform. This relative bioavailability or lack thereof may make these agents easier to formulate with a specific concentration of drug in solution, more effective, less effective or safer or less safe in treated patients with a disease. In particular, larger particle sizes or reduced surface area may be less soluble and, therefore, less bioavailable resulting in less systemic exposure and therefore better safety while maintain local activity and efficacy. In particular, treating patients with formulations made from some of these forms may result in reduced liver toxicity, reduced serotonin levels or reduced pressure in the lungs or a reduced chance of developing pulmonary arterial hypertension compared to more bioavailable particles such as those that may be found in *Indigo naturalis*.

The solid particles of the AhR agonist compound, such as indigo and/or indigo derivatives, can have average particles sizes of less than about 5000 nm, less than 3000 nm, less than 2000 nm or less than 1500 nm. In other embodiments, the solid particles of indigo and/or indigo derivatives can have average particles sizes of equal to or greater than about 1500 nm, 2000 nm, 2500 nm, 3000 nm or 5000 nm. In some embodiments, more than about 60%, 70%, 75%, 80%, 85% or 90% of the particles are larger than about 1500 nm, 2000 nm, 2500 nm, 3000 nm or 5000 nm. In some embodiments, more than about 60%, 70%, 75%, 80%, 85% or 90% of the particles are smaller than about 1500 nm, 2000 nm, 2500 nm, 3000 nm or 5000 nm. In some embodiments, the particles can contain optionally include a surface stabilizer, or may exclude a surface stabilizer. The particles may contain drug in suspension or fully dissolved. The particles may contain the AhR agonist compound in a crystalline form or amorphous form.

In some embodiments, the AhR agonist compound, such as indigo and/or indigo derivatives, can be bound to or mixed with particles that contain calcium carbonate, cellulose, organic resins, inorganic resins, clay or zeolites. In some embodiments, the indigo and indigo derivatives can be free from calcium carbonate or cellulose.

In some embodiments, the solid powder contains multiple active agents, such as indigo and/or one or more indigo derivatives, in the same particle or in the same population of particles. In some embodiments, the solid powder contains a mixture of distinct particles each comprising an active agent of indigo or a particular indigo derivative. In some embodiments the particles are at least about 95%, 96%, 97%, 98% or 99% pure or are over 99.9% pure. The solid particles can each have the same average particle size or can have different average particles sizes. In other embodiments, the solid particles may have the same solubility in a selected solvent (e.g., water or ethanol) or may have the same bioavailability.

In some embodiments, the composition differs in solubility or bioavailability from *Indigo naturalis* that contains the same amount of a given active agent (e.g., the AhR agonist compound, such as indigo or an indigo derivative or a prodrug thereof). This difference in solubility may be seen in solvents including water, low pH water, or certain formulation solvents, such as ethanol, n-methyl pyrrolidone, polyethylene glycol, or dimethylsulfoxide. This difference in solubility or bioavailability may be due to the particle surface area, particle size, particle shape, contaminants, purity and/or hydrophobicity of the particles or excipients included in a given formulation.

The AhR agonist compound, such as indigo, an indigo derivative, and/or prodrugs thereof, may be free from or reduced substantially of impurities. For example, when the AhR agonist compound is indigo, an indigo derivative, and/or a prodrug thereof, it is free of impurities found in *Indigo naturalis*. In some instances the impurity may be an allergen or toxin. In some embodiments the impurity may be butaedioic acid, isatin, 2,3-dihydro-4-hydroxy-2-oxo-1H-indole-3-acetic acid, deoxyvascinone, 10H-indolo [3,2-b] quinolone, 3-(2-hydroxyphenyl)-4-(3H)-quinazolinone, 10H-indolo[3,2-b]quinolone-11-carboxylic acid amide, tryptanthrin, syringin, 3-(2-carboxyphenyl)-4(3H)-quinazolinone, indigo, indican, indiruibin, 2-[cyano(3-indolyl) methylene]-3-indolone, octadecanoic acid, octadecanoic acid, bisindigotin, qingdainone, botulin, sugiol, rotenol, sitosterol, daucosterol, clerosterol, indospicine and/or 3-nitropropionate. In some embodiments the impurity may be inorganic, or may be a heavy metal, such as arsenic, cadmium, lead and/or mercury. The impurity may also be a pesticide, a herbicide, an aflatoxin, a solvent (such as water, ethanol, ethanol, THF, petroleum ether, chloroform or acetic acid), silicon dioxide, limestone, cellulose, or calcium carbonate. In one embodiment, the indigo and/or indigo derivative is substantially free of one or more of such impurities. In one embodiment, a composition comprising synthetic indirubin is contemplated, where the composition contains less than about 0.1 wt % of the impurities indigo, tryptanthrin and qingdianone. In another embodiment, a composition comprising synthetic indirubin is contemplated, where the synthetic indirubin is greater than 98 wt % pure synthetic indirubin. That is, the synthetic indirubin comprises less than about 2 wt % impurities. In other embodiments, the composition described herein is free of bacteria and extraction solvents.

It is also contemplated that the indigo, indigo derivative, and/or prodrugs thereof may have less bioburden per gram than *Indigo naturalis*, in some embodiments. For example, the indigo and/or indigo derivatives may have a reduced bacterial count, reduced yeast count, reduced mold count, reduced *e-coli* count and/or reduced salmonella count than a preparation or extract of *Indigo naturalis*. In some embodiments the indigo and indigo derivatives may be more resistant to the growth of microorganisms. In some embodiments the indigo and/or indigo derivatives may have less than about 15,000, 25,000, 35,000 or 50,000 colony-forming units per gram. In some embodiments the indigo and indigo derivatives may be sterile. In some embodiments the indigo and indigo derivatives may include a preservative that inhibits bacterial and/or microbe growth over time.

The indigo, indigo derivative, and/or prodrugs may differ in color than *Indigo naturalis* and may be more purple, red, dark blue, light blue or blackish. In some embodiments, the indigo and indigo derivatives may be purplish, reddish, orangish, pinkish, or brownish. In some embodiments, the indigo, indigo derivative, and/or prodrugs may be lighter in color, white or clear. The indigo, indigo derivative, and/or prodrugs may be reduced into their reduced forms changing their color or rendering them less colored or even colorless or white. In some embodiments, the indigo, indigo derivative, and/or prodrugs may have particle sizes in the nanometer range or may have a unique structure that alters their color compared to what is found in *Indigo naturalis* or what has been purified from synthetic preparations.

Indigo and indigo derivatives and prodrugs thereof are exemplary AhR agonists. As mentioned above, the compositions comprise an AhR agonist compound, and in one embodiment, the AhR agonist compound has a half maximal effective concentration ($EC_{50}$) of less than about 10 nM, 8 nM, 6 nM, 5 nM, 4 nM, 3 nM, 2 nM, 1 nM, 0.5 nM or 0.25 nM.

In one example the AhR agonist may be endogenously found in the plasma, liver, urine, on the skin or in the gut of the human body. These endogenous AhR agonists may be produced by the human body via the metabolism of foods, via exposure of precursors to UV light (including UVB) or via microbes that live on or in the human body.

Indigo and indigo derivatives and prodrugs thereof are exemplary kinase and transcription factor inhibitors. The compositions mentioned above can comprise agents that also inhibit a kinase or transcription factor. These kinase or transcription factors may be in a post-translationally modified or unmodified form including but not limited to being in a phosphorylated or unphosphorylated form. They may be free or associate with other enzymes or cofactors as part of a complex. In one embodiment the agents can be an inhibitor of a signal transducer and activator of transcriptions (STAT) such as STAT3, a Janus kinase (JAK) such as JAK2, a mitogen-activated protein kinase (MAPK) which includes extracellular signal-regulated kinase (ERK) such as ERK2, a tyrosine-protein kinase such as C-src tyrosine kinase, a casein kinase such as casein kinase 1, a cyclin-dependent kinase (CDK) such as CDK1, CDK2 or CDK5 or a glycogen synthase kinase (GSK) such as GSK3B at a half maximal effective concentration ($IC_{50}$) of less than about 100 µM, 50 µM, 25 µM, 10 µM, 5 µm or 1 µM.

Indigo and indigo derivatives (and their prodrugs) may also be cytotoxic to fast dividing cells. The compositions mentioned above can comprise agents that are cytotoxic to fast diving cell such as CD4+ T-cells at a half maximal effective concentration ($IC_{50}$) of less than about 100 µM, 50 µM, 25 µM, 10 µM, 5 µm or 1 µM.

As mentioned, the compositions also comprise a carrier or a pharmaceutically acceptable vehicle or excipient, to ease topical application or administration. In an embodiment, topical administration is preferred. In other embodiments, the composition can be oral and the carrier is selected for such oral administration. With regard to topical composition, the carrier will vary depending on the desired composition, which can take a number of different forms, including, for example, a solution, liquid, spray, foam, lotion, gel and the like. Preferably, the topical composition is a liquid, has good stability, adheres to the skin, and has a smooth feel. Information regarding suitable formulations is found, for example, in "Remington: The Science and Practice of Pharmacology," 22nd edition, (Pharmaceutical Press, 2013).

The compositions may also contain relatively small amounts, e.g., less than about 10% (w/w) of one or more auxiliary excipients suitable for topical use including but not limited to pH modifying agents, preservatives, thickening agents, gel-forming agents, emulsifying agents, antioxidants, scent agents, and the like. Compounds suitable for incorporation may be found, e.g., in R. C. Rowe, et al., *Handbook of Pharmaceutical Excipients* (4$^{th}$ Ed.), Pharmaceutical Press, London, 2003.

Gelling agents which may be used in the compositions include conventional gelling agents well known for their gelling properties, such as, for example, cellulose ethers such as hydroxypropyl cellulose, hydroxypropyl methylcellulose, carboxymethyl cellulose, sodium carboxymethyl cellulose, hydroxyethyl cellulose, and the like; vinyl alcohols; vinyl pyrrolidones; natural gums such as karaya gum, locust bean gum, guar gum, gelan gum, xanthan gum, gum arabic, tragacanth gum, carrageenan, pectin, agar, alginic acid, sodium alginate and the like, and methacrylates such as those available under the tradename Eudragit® from Rohm Pharma. Other gelling agents include polyoxyethylene—polyoxypropylene copolymers (poloxamers) such as those available under the tradename "Lutrol®", and the like. Preferred gelling agents are those absent free carboxyl groups such as, for instance, hydroxypropylcellulose, hydroxypropylmethylcellulose, hydroxyethylcellulose, methylcellulose, organo/cold water soluble cellulose, hydroxyethylmethylcellulose, ethylcellulose, ethyl(hydroxyethyl)cellulose. For substituted celluloses, a moderate to high degree of substitution is preferred, in some embodiments. A preferred degree of substitution is at least 1.0, or preferably in the range of 1.2 to 6.0, or more preferably in the range of 2.5 to 4.5.

The composition may also contain an antioxidant. The amount of antioxidant, if present, will typically range from about 0.005% to about 3.0% by weight of the composition. Illustrative ranges include from about 0.01% to about 2.5% by weight antioxidant, from about 0.05% to about 2% by weight antioxidant, and from about 0.1% to about 1.5% by weight anti-oxidant. Suitable antioxidants include, for example, butylated hydroxyanisole (BHA), ascorbyl palmitate, butylated hydroxytoluene (BHT), tertiary butyl hydroquinone, propyl gallate, α-tocopherol, sodium metabisulfite, and the like.

The composition may further contain one or more preservatives in an amount typically ranging from about 0.01% to about 2.0% by weight of the composition. Illustrative preservatives include, for example, phenoxyethanol, methyl paraben, propyl paraben, butyl paraben, benzyl alcohol, and the like. Other scents may include amyris, calone, coumarin, frangipani, muguet, narciussus and the like. Some scents may be derived from chemical such as eucalyptol, eugenol, geranyl acetate, linalool, nerolidol, thymol, or phenyl ethyl alcohol and the like.

The composition may also comprise a small amount, such as 0.1% to 10% by weight, of one or more compounds effective to introduce a favorable scent, fragrance, or aroma, such as a natural oil or other suitable agent. Suitable essential oils include, for example, plant essential oils from eucalyptus, frankincense, patchouli, peppermint, lemon, lavender, orange, rosehip, rosemary, tea tree, jasmine, and the like.

A composition in the form of a gel is contemplated. Gels are formed by the entrapment of large amounts of aqueous or aqueous-alcoholic liquids in a network of colloidal solid particles. These colloids are typically present at concentrations of less than 10% w/w and are also referred to as gelling agents or thickening agents, also mentioned herein above. Examples of gelling agents include carboxymethyl cellulose, hydroxypropylmethyl cellulose, hydroxyethyl cellulose, methyl cellulose, sodium alginate, alginic acid, pectin, carrageen, agar, clays, aluminum silicate, carbomers, etc. An exemplary gelling agent is hydroxypropyl cellulose. Hydroxypropylcelluloses having a weight average molecular weight between about 50,000 to 150,000 Daltons, or from about 60,000 to about 125,000 Daltons, or preferably from about 80,000 to about 100,000 Daltons, are exemplary.

Various other structural matrix formers can be added to the composition, for example hydrocarbons such as white petrolatum (petroleum jelly, Vaseline®), yellow petrolatum (petroleum jelly), paraffin (paraffin wax, hard paraffin), microcrystalline wax, ceresin (mineral wax, purified ozokerite); silicones; silicates such as fumed silica (CAB-O-SIL), bentonite (colloidal aluminum silicate), and veegum (colloidal magnesium aluminum silicate); polyols and polyglycols such as solid polyethylene glycol; sterols and sterol esters such as cholesterol, lanolin, anhydrous lanolin, and semisynthetic lanolin; and esters or polyesters such as bees wax, white bees wax (bleached bees wax), Carnauba wax, cholesterol esters (stearate), lard or hydrogenated oils.

The composition can also be in the form of a cream. Creams are emulsions of oleaginous substances and water (i.e. the carrier). The cream may be a water-in-oil (w/o) in which an aqueous phase is dispersed in an oil phase, or an oil-in-water (o/w) which have an oil dispersed within an aqueous base.

An ointment is also contemplated, and is typically more viscous than an o/w cream and may be free from water. Traditional ointment bases (i.e. the carrier) include hydrocarbons (petrolatum, beeswax, etc.), vegetable oils (e.g., canola oil, olive oil), fatty alcohols (cholesterol, lanolin, wool alcohol, stearyl alcohol, etc.), PEGs or silicones. Ointments may have drug fully in solution or fully or partially in suspension.

Pastes are a type of formulation into which a high percentage of insoluble particulate solids have been added, up to 50% by weight. Insoluble solids such as starch, zinc oxide, calcium carbonate, or talc may be used. In one embodiment, the composition does not comprise one or more of olive oil, wax, or petroleum jelly. In another embodiment, the composition is not an ointment.

The topical composition can also be a foam or an aerosolized or aerosolizable composition. The formulation may be dissolved in a propellant and a co-solvent such ethanol, acetone, hexadecyl alcohol, etc. Foaming agents may be incorporated to produce a mousse or a shampoo.

The composition may also be prepared to be in a solid form, such as a bar or stick that can be rubbed onto the skin. The compositions, whether liquid, cream, ointment or solid, may be used in an application device that permits application of the composition to a target site on the skin. For example, a device may be employed that allows the composition to be applied without first applying the composition to one's fingers. Suitable devices include spatulas, swabs, syringes without needles, plasters, and adhesive patches. Use of spatulas or swabs, or the like may require the device to be inserted into a container containing the composition. Using syringes or brushes or swabs may be accomplished by filling the syringe or brush or swab with the formulation. The composition may then be topically spread by the device, or may be expelled from the device onto the desired location of a person's skin.

A wide variety of methods may be used for preparing the compositions described above. Broadly speaking, the compositions may be prepared by combining together the components at a temperature and for a time sufficient to provide a pharmaceutically effective and elegant composition. The term "combining together", as used herein, means that all of the components of the compositions may be combined and mixed together at about the same time. The term "combining together" also means that the various components may be combined in one or more sequences to provide the desired product. The formulation can be prepared on a weight/weight (w/w) or a weight/volume (w/v) basis depending upon the form of the final dosage form.

Studies were conducted by preparing exemplary compositions comprised of synthetic indirubin as a model AhR agonist. The compositions were prepared with indirubin incorporated into a carrier suitable for topical application to the skin. In a first study, detailed in Example 2, twenty topical formulations were prepared. The formulation components are summarized in Table A, and details of the components are shown in Tables 2-1, 2-2 and 2-3 of Example 2.

TABLE A

Exemplary Compositions

| Formulation Id. No. | Synthetic indirubin (wt %) | Oily Liquid (e.g., oil, oleic acid, diethyl sebacate, lanolin, PEG) (~wt %) | Solvent(s) (~wt %) | Wax (e.g. beeswax, paraffin) (~wt%) | Surfactants/ Thickeners |
|---|---|---|---|---|---|
| OO02 | 0.025 | ~66 | ~18 | ~17 | — |
| OO09 (0.08%) | 0.08 | ~63 | ~20 | ~17 | — |
| OO09 (0.20%) | 0.20 | ~63 | ~20 | ~17 | — |
| OO14 | 0.08 | ~53 | ~30 | ~17 | — |
| OO17 | 0.20 | ~66 | ~17 | ~17 | — |
| OO19 | 0.20 | ~62 | ~21 | ~17 | — |
| OO29 | 0.02 | ~25 | ~25 | ~50 | — |
| OO40 | 0.02 | ~53 | ~30 | ~17 | — |
| OO54 | 0.02 | ~24 | ~34 | ~27 | ~15 |
| OO61 | 0.14 | ~10 | ~27 | ~48 | ~15 |
| OO65 | 0.01 | ~20 | ~22 | ~53 | ~4 |
| OO66 | 0.012 | ~20 | ~22 | ~53 | ~4 |
| OO67 | 0.36 | ~20 | ~18 | ~58 | ~4 |
| OO73 | 0.10 | ~9 | ~60 | ~22 | ~9 |
| OO75 | 0.02 | ~25 | ~25 | ~50 | — |
| OO76 | 0.02 | ~25 | ~25 | ~50 | — |
| OO77 | 0.016 | ~10 | ~27 | ~47 | ~15 |
| PO01 | 0.11 | ~70 | ~30 | — | — |
| PO03 | 0.11 | ~80 | ~20 | — | — |
| 438S | 0.02 | ~83 | — | ~17 | — |

The formulations were prepared by first adding synthetic indirubin and any antioxidant(s) into the non-oleaginous solvent(s) to either dissolve or suspend the synthetic indirubin in the solvent(s) before addition of the other components—the oleaginous component and the wax component were first heated to about 75° C. before addition. The exemplary formulations comprised between about 0.001-0.5 wt %, 0.001-0.4 wt %, 0.001-0.3 wt %, 0.001-0.25 wt %, 0.002-0.5 wt %, 0.002-0.4 wt %, 0.002-0.3 wt %, 0.002-0.25 wt %, 0.005-0.5 wt %, 0.005-0.4 wt %, 0.005-0.3 wt %, 0.005-0.25 wt %, 0.01-0.5 wt %, 0.01-0.4 wt %, 0.01-0.3 wt %, 0.01-0.25 wt % indirubin (synthetic or natural). In one embodiment, the composition comprises more than about 0.01 wt % indirubin and equal to or less than about 0.4 wt %, 0.3 wt % or 0.2 wt % indirubin.

In formulation identification nos. OO14 and PO03, which each comprised at least about 20 weight percent of dimethylsulfoxide as a solvent, the indirubin was in dissolved form. That is, the synthetic indirubin was fully solubilized in the composition. Formulation identification no. OO02 comprising 0.025 wt % indirubin and about 18 wt % of a solvent system (diethylene glycol monoethyl ether, n-methyl-2-pyrrolidone, and isopropyl myristate) also provided a final composition where the indirubin was in solution (or fully solubilized) in the composition (at room temperature of 23-25° C.). In one embodiment, a topical composition comprises between about 0.025-0.30 weight percent, 0.25-0.25 weight percent, 0.075-0.30 weight percent, or 0.75-0.25 weight percent synthetic indirubin, where the indirubin is essentially fully dissolved, essentially completely dissolved, or is fully or completely dissolved in the composition. Stated alternatively, the indirubin is in solution in the composition, as evidenced, by example, no visible particles of the agent when inspected with the human eye and/or microscopically. The composition, in an embodiment, comprises between about 2.5-50 wt %, 2.5-35 wt %, 5-50 wt %, 5035 wt %, 15-35 wt %, 17-32 wt %, 18-32 wt %, 19-31 wt %, or 20-30 wt % of a solvent selected from dimethylsulfoxide, n-methyl-2-pyrrolidone, diethylene glycol monoethyl ether, isopropyl myristate, glycerol, and/or propylene glycol.

Accordingly, in embodiments the composition comprises an oily liquid (or an oleaginous compound) and/or a polyethylene glycol polymer (preferably with a molecular weight of between about 2500-10,000 Daltons, 2500-8000 Daltons, 2500-7500 Daltons, 2500-6000 Daltons, 2500-5000 Daltons, 3000-4500 Daltons or 3500-4500 Daltons). In one embodiment, the oily liquid is, for example, a synthetic oil, a vegetable oil or an animal fat. In certain embodiments, the oily liquid is mineral oil, oleic acid, olive oil, castor oil, jojoba oil or lanolin. In one embodiment, the oily liquid (or oleaginous compound) is a liquid at ambient temperature (e.g., 23-25° C.). Exemplary oily liquids include oleic acid and diethyl sebacate. In one embodiment, the oleaginous compound is a petrochemical based compound. That is, it is not of animal or vegetable origin. In another embodiment, the oleaginous compound is a synthetic compound or a petrochemical based compound that comprises at least 9, 10, 11, 12, 13, 14, 15, 16, 17, 18 or 20 carbon atoms. In one embodiment, the composition does not comprise olive oil. In one embodiment, the composition does not comprise castor oil. In an embodiment, the oily liquid is present in the composition in an amount between about 8-90 wt %, 15-80 wt %, 15-75 wt %, 15-70 wt %, 15-65 wt %, 20-80 wt %, 20-75 wt %, 20-65 wt %, 20-60 wt %, or 20-55 wt %.

In an embodiment, the composition optionally comprises a wax component. The amount of wax component in the composition, when present, is between about 8-65 wt %, 10-55 wt %, 12-60 wt %, 12-50 wt %, 12-45 wt %, 12-40 wt %, 12-35 wt %, 12-25 wt %, 15-60 wt %, 15-55 wt %, 15-50 wt %, 15-45 wt %, 15-40 wt %, 15-35 wt %, 15-25 wt %, 16-55 wt %, 16-50 wt %, 16-45 wt %, 16-40 wt %, 16-35 wt %, or 16-25 wt %. In one embodiment, the wax component is a solid at ambient temperature (e.g., 23-25° C.). In one embodiment, the wax component is selected from beeswax, paraffin wax (e.g., $C_nH2_{n+2}$, n=20-30), cetyl alcohol, alkyl silicones, and lanolin wax. In one embodiment, the composition does not comprise beeswax. In another embodiment, the wax component is a synthetic wax; that is the wax is not one produced by nature, but is manufactured chemically in a laboratory or industrial process.

Contemplated compositions, in another embodiment, are comprised of at least about 25 wt % and less than about 99 wt % of an oily liquid and a wax component. In certain embodiments, the oily liquid and wax component comprise less than about 95 wt %, 90 wt %, 85 wt %, 75 wt %, 70 wt %, 65 wt % or 55 wt % of the composition and greater than about 25 wt %, 30 wt %, 35 wt %, 40 wt %, 45 wt % or 50 wt %.

In one embodiment, the composition further comprises a solvent, where the solvent can be a single solvent or a combination (or mixture) or two or more solvents. In one embodiment, the solvent is an aprotic solvent, and can be either water miscible, partially water miscible, or poorly water miscible. In one embodiment, the solvent is non-oleaginous. It is also desired that the solvent be non-toxic. Non-limiting examples of aprotic solvents are set forth in Table B.

TABLE B

Exemplary Aprotic Solvents

| Solvent | Class | Water Miscibility | Dipole Moment (D) |
| --- | --- | --- | --- |
| 2-pyrrolidone | amides | | 3.5 |
| dimethyl formamide | | water miscible | 3.86 |
| N-methyl-2-pyrrolidone (NMP) | | water miscible | 4.09 |
| n-ethyl-2-pyrrolidone | | water miscible | 4.1 |
| dimethyl acetamide | | water miscible | 4.60 |
| N-cyclohexyl-2-pyrrolidone | | poorly miscible | |
| caprolactam (cyclic amide) | | | |
| ethyl acetate | esters of a carboxylic acid | partially miscible (8.3 g/100 ml) | 1.84 |
| benzyl benzoate | | poorly miscible | 2.06 |
| methyl acetate | | water miscible | 1.75 |
| isopropyl myristate | Esters of a fatty acid | poorly miscible | |
| ethyl oleate | | poorly miscible | |
| methyl lactate | Esters of an acid (monobasic acid) | water miscible | |
| ethyl lactate | | water miscible | |
| propylene carbonate (4-methyl-1,3-diololan-2-one) | Esters of an alcohol (polyhydroxy alcohol) | water miscible | 4.9 |
| dimethyl ether | ethers | | 1.25 |
| tetrahydrofuran | | water miscible | 1.75 |
| methyl ethyl ketone | ketones | water miscible (27.5 g/100 mL) | 2.76 |
| acetone | | water miscible | 2.77 |
| butyrolactone | lactones | water miscible | 4.12 |
| ester-caprolactone | | water miscible | 3-4 |
| dimethyl sulfoxide | sulfoxides | water miscible | 3.9 |
| decylmethylsulfoxide | | | 3.96 |

In one embodiment, the aprotic solvent is a solvent with a dipole moment of greater than about 2.5 D, or greater than about 3.0 D, or greater than about 3.5 D. In one embodiment, the aprotic solvent is a solvent with a dipole moment of greater than about 2.5 D, or greater than about 3.0 D, or greater than about 3.5 D and is water miscible. In another embodiment, the aprotic solvent is a solvent with a dipole moment of greater than about 2.5 D, or greater than about 3.0 D, or greater than about 3.5 D and is poorly miscible in water. In one embodiment, a solvent is miscible with water if it forms a homogeneous solution with water in all proportions at room temperature (20-25° C.). A solvent is partially miscible if it forms a homogeneous solution with water in some proportions at room temperature (20-25° C.). A solvent is poorly miscible if it does not form a homogeneous solution with water (20-25° C.). In one embodiment, the solvent is a dipolar aprotic solvent.

The aprotic solvent can be one from a class of solvents selected from the group consisting of an amide, an ester of an acid, an ester of an alcohol, an ether, a ketone, a lactone and a sulfoxide. With reference to Table B, solvents in the class of amide solvents includes 2-pyrrolidone, dimethyl formamide, N-methyl-2-pyrrolidone, N-ethyl-2-pyrrolidone, dimethyl acetamide, n-cyclohexyl-2-pyrrolidone and caprolactam. Solvents in the class of esters of acids include, for example, carboxylic acid esters and fatty acid esters, such as ethyl acetate, benzyl benzoate, methyl acetate, isopropyl myristate, ethyl oleate, methyl lactate and ethyl lactate. Aprotic solvents that are esters of an alcohol include propylene carbonate (4-methyl-1,3-diololan-2-one). The aprotic solvents in the sulfoxide class include dimethyl sulfoxide and decylmethylsulfoxide.

In another embodiment, the solvent has a molecular weight of less than about 150 g/mol, less than about 125 g/mol, less than about 110 g/mol, less than about 100 g/mol, less than about 90 g/mol. For example, DMSO has a molecular weight of about 78 g/mol and NMP has a molecular weight of 99 g/mol.

In one embodiment, the solvent is an aprotic solvent selected from the group consisting of dimethylsulfoxide, n-methyl-2-pyrrolidone, diethylene glycol monoethyl ether, and isopropyl myristate. In another embodiment, the solvent is selected from glycerol and propylene glycol.

In some embodiments, the solvent is not caprylic/capric triglyceride, glyceryl dibehenate, tribehenin or glyceryl behenate, glyceryl stearate, PPG-15 steryl ether, water, glycerol, ethanol, propylene glycol, butylene glycol, dipropylene glycol, an ethoxylated or propoxylated diglycol, or a cyclic polyol.

As mentioned above, the AhR agonist, such as indirubin (synthetic or natural), can be suspended or dissolved in the solvent system and/or in the composition. In one embodiment, the AhR agonist is dissolved in the solvent system and in the composition, so that no crystalline or particulate form of the AhR agonist is observed (visually or via XRPD) in the composition. In another embodiment, the AhR agonist is dissolved in the solvent system so that no crystalline or particulate form of the AhR agonist is observed (visually) in solvent system, and the AhR agonist may or may not be dissolved or in solution in the composition.

The compositions optionally include a surfactant or a thickening agent. The surfactant can be an ionic or non-ionic surfactant, and in one embodiment is a non-ionic triblock copolymer surfactant, such as a poloxamer. In another embodiment, a thickening agent is included in the composition, and exemplary agents include but are not limited to polymers such as poly-celluloses, polyacrylamides, polyacrylic acids, polyvinylpyrrolidones, as well as other known agents such as guar gum. Polycelluloses include hydroxyalkyl celluloses, such as hydroxypropylcellulose, hydroxymethylcellulose, hydroxyethylcellulose. Acrylic and methacrylic acid polymer and copolymers include polyacrylic acid and polymethacrylic acid. Polyacrylamides include polyacrylamide (poly(2-propenamide) and copolymers with polyacrylamide, including the copolymer dispersion hydroxyethyl acrylate/sodium acryloyldimethyl taurate copolymer (SEPINEO™ P600).

In one embodiment, the composition is essentially free of water. In another embodiment, the composition comprises less than about 2 wt %, 1 wt %, 0.5 wt % or 0.025 wt % water. In another embodiment, the composition is essentially free of water and comprises between about 0.01-0.5 wt %, 0.01-0.4 wt %, 0.01-0.3 wt %, 0.01-0.25 wt %, 0.05-0.5 wt %, 0.05-0.4 wt %, 0.05-0.3 wt %, 0.05-0.25 wt %, 0.075-0.5 wt %, 0.075-0.4 wt %, 0.075-0.3 wt %, 0.075-0.25 wt % indirubin (synthetic or natural).

In another embodiment, the compositions described herein are physically and or chemically stable for at least about two months, four months, six months or twelve months upon storage at about 25° C. In an embodiment, chemically stable intends that the amount of indirubin does change, for example due to degradation, by more than 1%, 2%, 3%, 4% or 5% after two months, four months, six months or twelve months of storage at 25° C. In an embodiment, physically stable intends that the physical state of the formulation does not change, for example due to separation into distinct phases, or exhibit agglomeration or precipitation after two months, four months, six months or twelve months of storage at 25° C.

The compositions in Table A were tested in vitro to measure epidermal, dermal and transdermal skin penetration. As described in Example 2, human cadaver skin was placed on an in vitro diffusion apparatus with the stratum corneum side facing up. A known amount of about 10 mg of each formulation was applied to the defined skin surface area to provide a dose of about 10 mg/cm$^2$. Samples of the receptor fluid below the skin sample were taken to measure skin flux of the active agent over the 24-hour test period. After 24 hours, residual formulation was removed from the skin, the stratum corneum was removed from the skin, and the epidermis and dermis were separated. The amount of the AhR agonist indirubin in each of the epidermis, dermis and receptor solution was determined. Results are shown in Tables 1A-1C and in FIGS. 1A-1B.

FIG. 1A shows the mean amount of drug recovered, in ng, in the epidermis (open bars) and dermis (bars with cross-hatch fill) for each formulation. Formulation identification nos. OO09, OO14, OO17 and PO01 delivered more than 50 ng of synthetic indirubin (as a model AhR agonist) into the epidermis in the 24 hour test period. Formulation identification no. OO14 delivered in the 24 hour more than 50 ng of synthetic indirubin into both the epidermis and dermis, with more drug present in the dermis than the epidermis. Accordingly, in one embodiment, a composition that provides for topical administration of an AhR agonist, such as synthetic indirubin, for delivery to the dermis and the epidermis is contemplated, wherein the amount of agonist in the dermis 24 hours after topical application of the composition, is within 25%, 20%, 15%, or 10% of the amount in the epidermis. In preferred embodiments, the amount of agonist in the dermis 24 hours after topical application of the composition is equal to or at least about 5%, 10% or 15% greater than the amount in the epidermis.

Figure 1B:
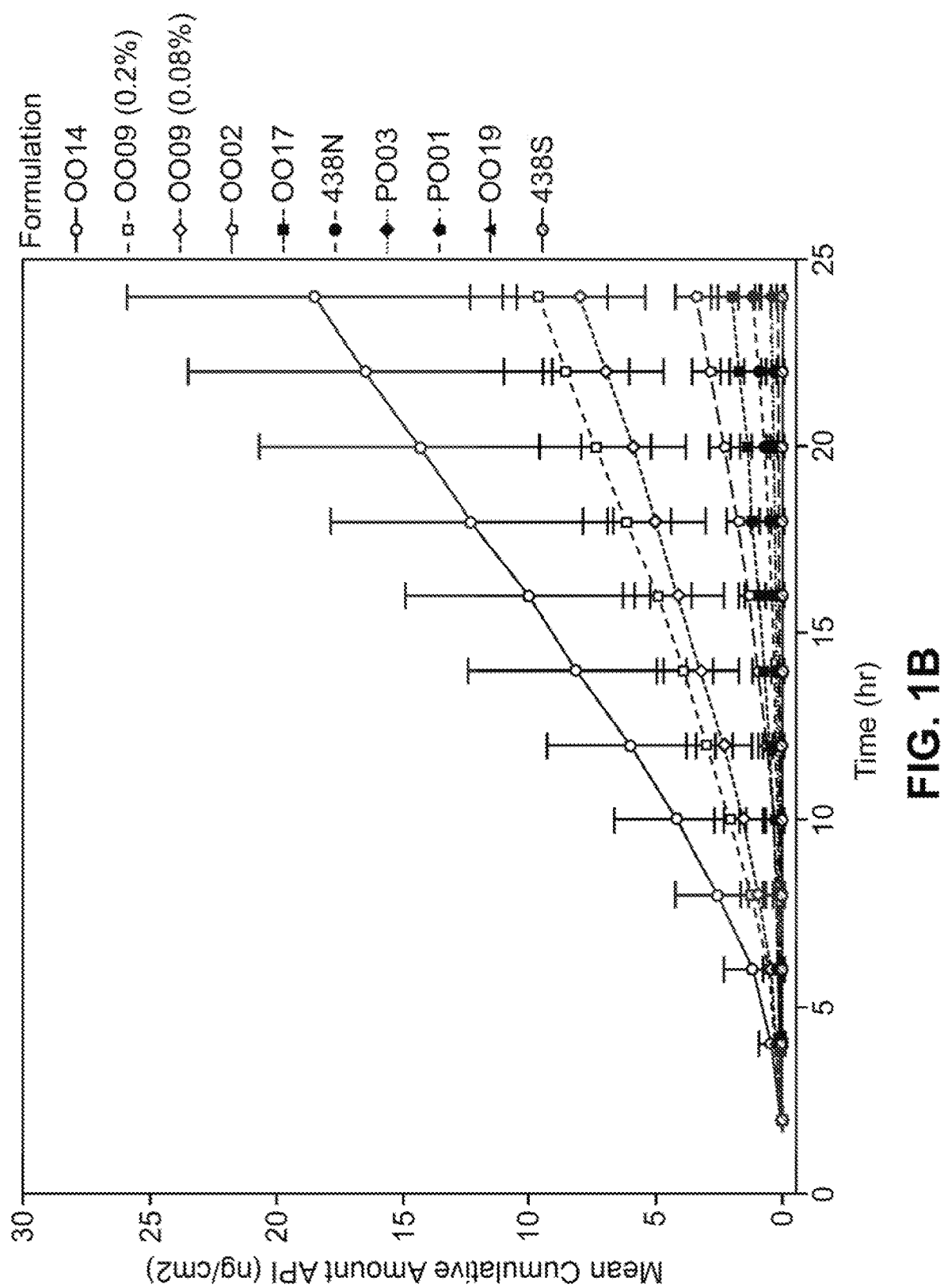
FIG. 1B is a graph showing mean cumulative amount of drug, in $ng/cm^2$, in receptor solution, as a function of time, in hours, for ten formulations prepared and tested as described herein.

FIG. 1B shows the mean cumulative amount of drug, in ng/cm$^2$, in receptor solution, as a function of time, in hours, for each formulation. Formulation identification no. OO14 yielded a flux of greater than about 5 ng/cm$^2$ 10 hours after topical application to skin and greater than about 12 ng/cm$^2$ 20 hours after topical application to skin and greater than about 15 ng/cm$^2$ 24 hours after topical application to skin. Accordingly, in one embodiment, a composition that provides an in vitro skin flux (using human cadaver skin) of at least about 5 ng/cm$^2$ 10 hours after topical application to the skin is contemplated. In other embodiments, compositions that provide an in vitro skin (human cadaver skin) flux of at least about 5 ng/cm$^2$ 10 hours after topical application to the skin and of at least about at least about 15 ng/cm$^2$ 25 hours after topical application to the skin is contemplated.

TABLE 1A

Mean amount of indirubin (ng) recovered from epidermis and dermis following 24 hours of in vitro application to human skin of the identified formulation.

| | Epidermis (ng) | | | Dermis (ng) | | |
|---|---|---|---|---|---|---|
| Formulation | N | Mean | Std Dev | N | Mean | Std Dev |
| OO02 | 5 | 32.3 | 7.3 | 5 | 30.6 | 6.8 |
| OO09 (0.08%) | 5 | 62.0 | 15.5 | 5 | 31.4 | 5.9 |
| OO09 (0.2%) | 5 | 88.6 | 19.4 | 5 | 34.6 | 7.6 |
| OO14 | 5 | 60.6 | 12.9 | 5 | 81.9 | 18.6 |
| OO17 | 5 | 82.7 | 40.0 | 5 | 24.6 | 9.1 |
| OO19 | 5 | 38.0 | 22.9 | 4 | 22.5 | 14.2 |
| PO01 | 5 | 76.3 | 15.5 | 4 | 10.2 | 0.4 |
| PO03 | 4 | 41.5 | 4.3 | 5 | 13.7 | 8.8 |
| 438N | 4 | 14.7 | 5.6 | 4 | 16.9 | 4.9 |
| 438S | 5 | 6.2 | 1.9 | 4 | 4.0 | 1.0 |

TABLE 1B

Indirubin molarity in the dermis and epidermis following 24 hours of application in vitro to human skin of the identified formulation

| Formulation | Dermis (µM) | Epidermis (µM) |
|---|---|---|
| OO02 | 1.2 | 14.3 |
| OO09 (0.08%) | 1.2 | 27.5 |
| OO09 (0.2%) | 1.4 | 39.3 |
| OO14 | 3.3 | 26.9 |
| OO17 | 1.0 | 36.7 |
| OO19 | 0.9 | 16.8 |
| PO01 | 0.4 | 33.8 |
| PO03 | 0.5 | 18.4 |
| 438N | 0.7 | 6.5 |
| 438S | 0.2 | 2.7 |

TABLE 1C

Mean cumulative amount (ng/cm$^2$) and flux of indirubin (ng/cm$^2$/hr) at 24 hours following 24 hours of in vitro application to human skin of the identified formulation.

| Formulation | Cumulative amount of indirubin (ng/cm$^2$) | | | Indirubin Flux (ng/cm$^2$/hr) | | |
|---|---|---|---|---|---|---|
| | N | Mean | Std Dev | N | Mean | Std Dev |
| OO14 | 5 | 18.47 | 7.44 | 5 | 1.014 | 0.229 |
| OO09 (0.2%) | 5 | 9.62 | 2.72 | 5 | 0.548 | 0.134 |
| OO09 (0.08%) | 5 | 7.98 | 2.51 | 5 | 0.523 | 0.206 |
| OO02 | 5 | 3.37 | 0.84 | 5 | 0.266 | 0.073 |
| OO17 | 5 | 1.93 | 0.86 | 5 | 0.143 | 0.034 |
| 438N | 4 | 1.10 | 0.68 | 4 | 0.100 | 0.044 |
| PO03 | 5 | 0.50 | 0.32 | 5 | 0.060 | 0.041 |
| PO01 | 5 | 0.47 | 0.44 | 5 | 0.038 | 0.035 |
| OO19 | 4 | 0.08 | 0.16 | 4 | 0.013 | 0.027 |
| 438S | 5 | 0.00 | 0.00 | 5 | 0.000 | 0.000 |

In other embodiments, a composition that provides an in vitro skin (human cadaver skin) delivery of at least about 0.7 µM of indirubin into the dermis at 24 hours is contemplated. In another embodiment, a composition that provides an in vitro skin (human cadaver skin) delivery of at least about or more than about 6.5 µM of indirubin into the epidermis at 24 hours is contemplated. In another embodiment, a composition that provides an in vitro skin (human cadaver skin) a mean flux of greater than about 0.1, 0.3, or 0.5 ng/cm$^2$/hr of indirubin is contemplated. In one embodiment, the mean indirubin in vitro flux of greater than about 0.1, 0.3, or 0.5 ng/cm$^2$/hr of indirubin is though the top 500 microns of human skin.

The data in FIGS. 1A-1B and in Tables 1A-1C show that formulation identification no. 483N, which comprised a natural form of indirubin, had superior performance in the in vitro penetration assay compared to formulation identification no. 483S, which comprised synthetic indirubin, even though they both contained the same excipients and the same total amount of indirubin. This may be due to the fact that approximately four fold more of the indirubin in formulation identification no. 483N was in solution than in formulation identification no. 483S. Also, the methods of manufacturing the two formulations differed. Formulation identification no. 483N was made from *Indigo naturalis*, which contains indirubin as part of a complex solid mixture whereas formulation identification no. 483S was made from highly pure crystalline, synthetic indirubin.

Formulation identification no. OO09 (0.08%) and OO09 (0.2%) had approximately similar concentrations of indirubin in the dermis and receptor solution (FIG. 1B and Table 1C) despite an about 2.5 fold difference in amount of indirubin in the composition. This data supports that amount of indirubin in solution in the composition is a factor that relates to indirubin skin flux, and compositions wherein indirubin is essentially completely dissolved or fully dissolved achieve skin flux sufficient for treatment of the conditions described herein, and provide delivery of a therapeutically effective amount of indirubin into the epidermis and dermis.

Example 3 describes exemplary formulations using another AhR agonist, tapinarof. The tapinarof compositions are suitable for treatment of any of the conditions described herein, including psoriasis (Ps), atopic dermatitis (AD), contact dermatitis, hidradenitis suppurativa (HS), pyoderma gangrenosum (PG), Sweet's syndrome, mutations in the PSTPIP-1 gene (PAPA syndrome, PAPSH syndrome and PASH syndrome), Bechet's disease, bullous pemphigold, mucous membrane pemphigold, pemphis vulgaris, cutaneous Crohn's disease, Sjögren syndrome, systemic lupus erythematosus, prurigo nodularis (PN), pityriasis lichenoides chronica, palmoplantar pustulosis (PPP), pyoderma gangrenosum (PG) and erythoderma.

Example 5 describes results of a study on the pharmacodynamics of composition identified as formulation identification no. OO14. In this study, human skin placed on a static in vitro diffusion cell and a fixed amount of the formulation was applied to the skin. The formulation was applied to the skin at either 16 hours prior to or both 40 hours and 16 hours prior to Th17 stimulation. The receptor solution was replaced with the Th17 stimulation media was incubated for 24 hours prior to harvesting. The Th17 stimulation media contained a mixture of cytokines and antibodies that induce Th17 polarization (Smith S. H. et al., PLoS ONE 11(2): 0147979). qPCR was used to measure cytokine levels in the skin compared to an internal standard of GAPDH, and CYP1A1 was chosen as an indicator for AhR activation as it is poorly expressed under normal conditions and upregulated by activated AhR. IL-17alpha, IL-1beta, S100A7 and IL-8 are pro-inflammatory cytokines or antimicrobial molecules associated with Th17 type inflammation and are upregulated in HS lesions (Frew et al., F1000 Research 2018, 7:1930). As a control, 0.01% betamethasone (BMV) was added to the receptor solution at both 40 hours and 16 hours prior to Th17 stimulation. Results are shown in Table 2 and in FIGS. 2A-2E.

TABLE 2

Changes in Analyte Levels

| Formulation | Treatment Regimen | % Inhibition Compared to Th17 | | | |
|---|---|---|---|---|---|
| | | IL17-alpha | IL1-beta | S100A7 | IL8 |
| OO14 | 16 hours | 73.4 | 5.41 | 49.74 | 30.62 |
| OO14 | 16 hours & 40 hours | 91.57 | 53.48 | 76.49 | 53.22 |
| 0.01% BMV | | 96.99 | 58.66 | N/I* | 14.01 |

*N/I = Not Inhibited compared to Th17

FIGS. 2A-2E are bar graphs showing the percent activity of in human cadaver skin of CYP1A1 (FIG. 2A), IL17-alpha (FIG. 2B), IL1-beta, (FIG. 2C), IL8 (FIG. 2D), and S100A7 (FIG. 2E), each a biomarker of AhR modulation, where percent activity was calculated as percent decrease of the specified biomarker compared to Th17 stimulation, for a topical formulation identified herein as "OO14" comprising synthetic indirubin and applied to the skin for 16 hours or 40 hours before stimulation; formulation "BMV" is a control formulation of betamethasone steroid which was applied to the receptor solutions and inhibited expression of the biomarkers except for the antimicrobial peptide S100A7.

Figures 2A, 2B:
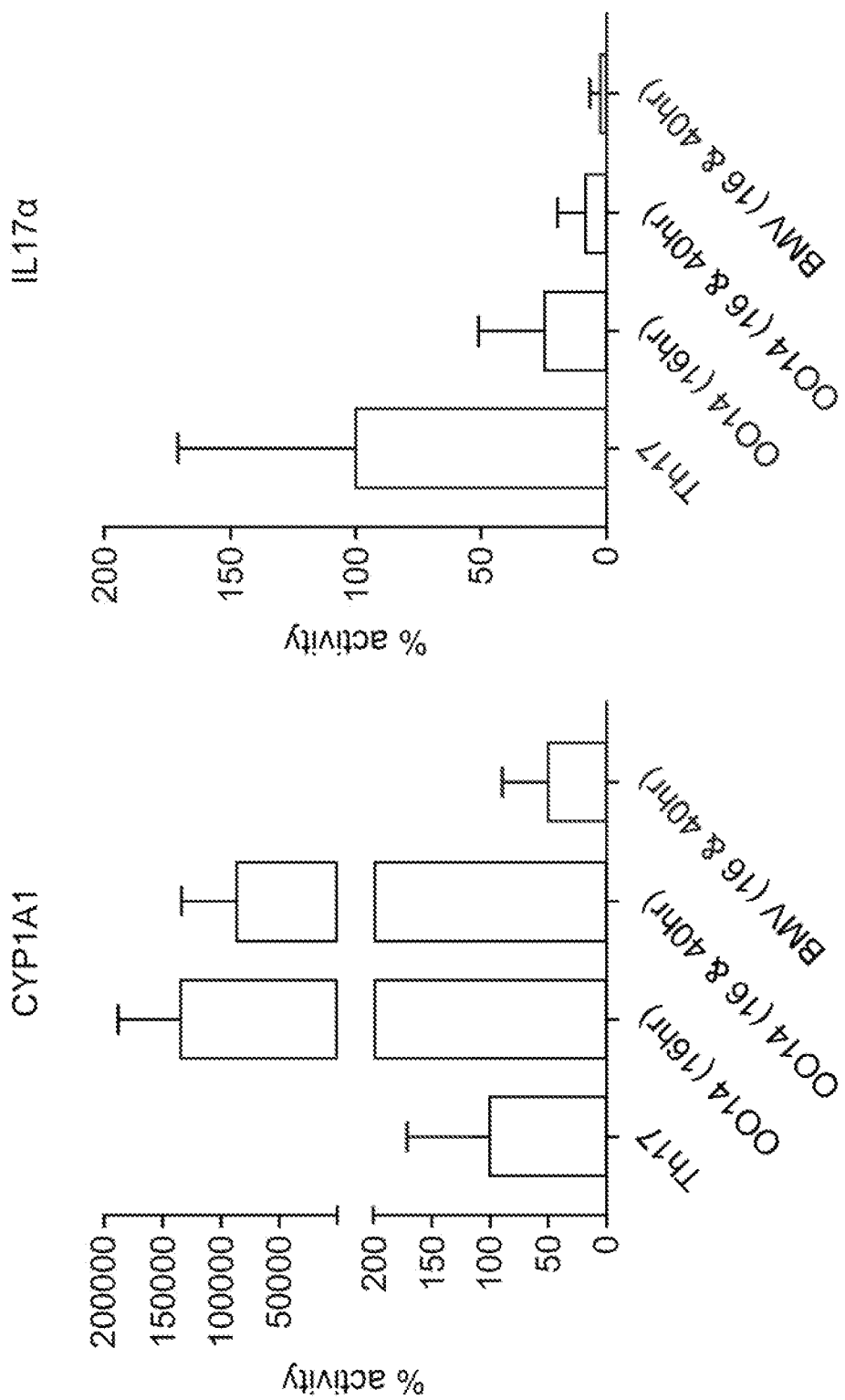
FIGS. 2A-2E are bar graphs showing the percent activity of in human cadaver skin of CYP1A1 (FIG. 2A), IL17-alpha (FIG. 2B), IL1-beta, (FIG. 2C), IL8 (FIG. 2D), and S100A7 (FIG. 2E), each a biomarker of AhR modulation or an anti-inflammatory or antimicrobial response, where percent activity was calculated as percent increase or decrease in stimulation of the specified biomarker compared to Th17 stimulation, for a topical formulation identified herein as "OO14" comprising synthetic indirubin and applied to the skin for a total of 16 hours or for 40 hours before a 24 hour stimulation (applied at both 40 hours and 16 hours before polarization); formulation "BMV" is a control formulation of betamethasone steroid, an inhibitor of the biomarkers except for the antimicrobial peptide S100A7.
Figure 2D:
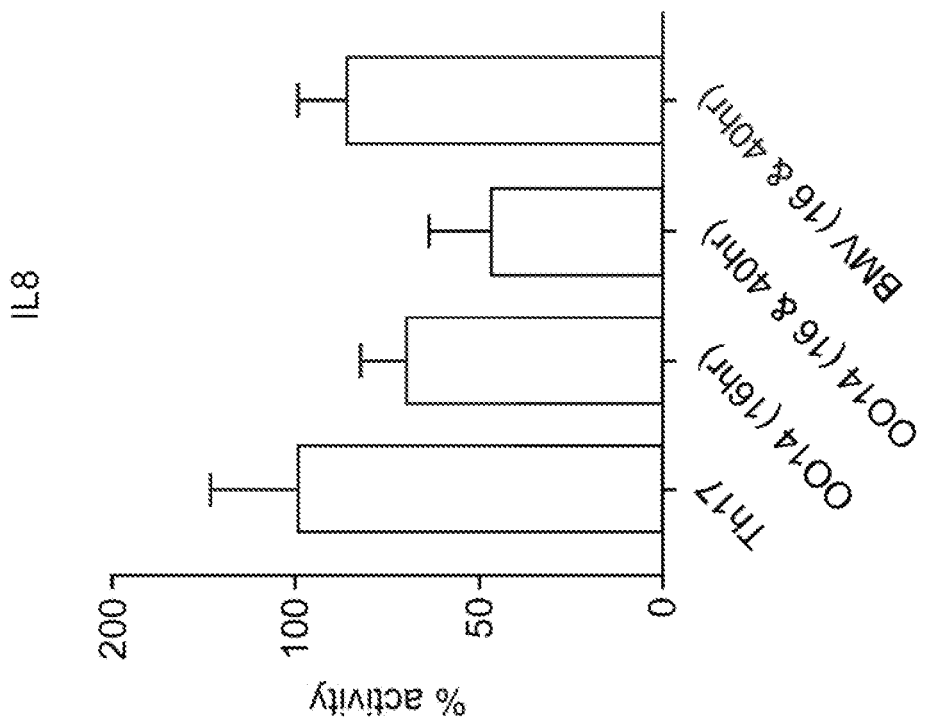
Figure 2C:
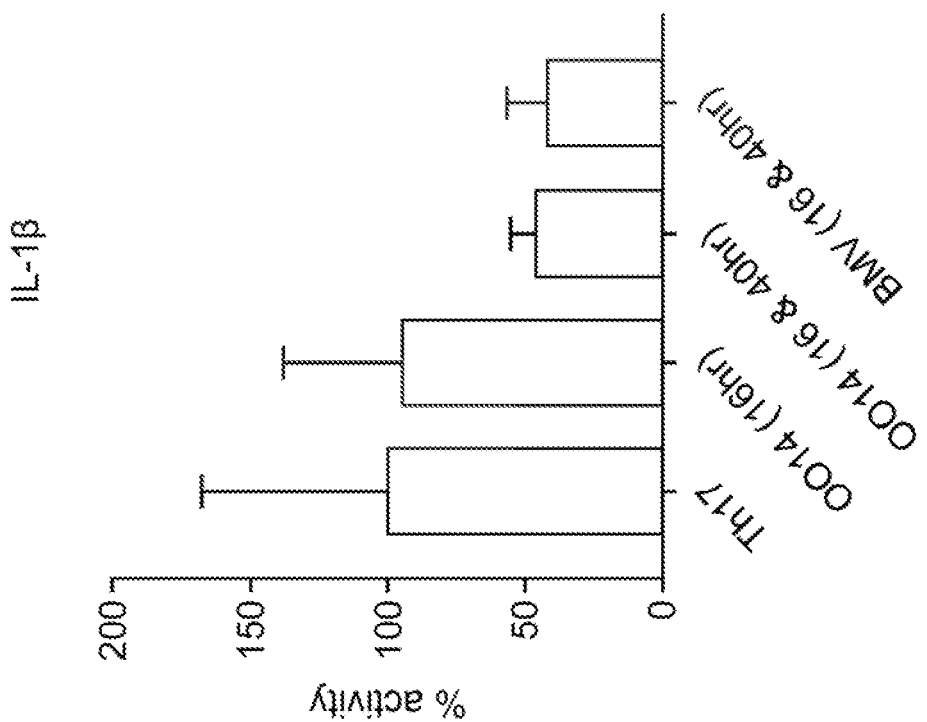
Figure 2E:
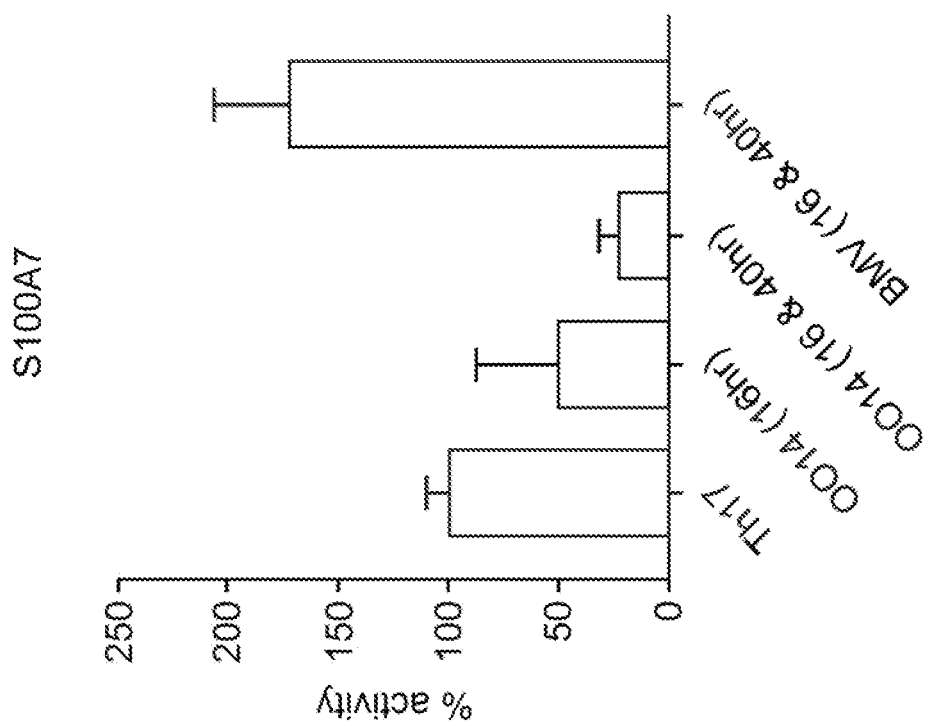

FIG. 2A shows that topical administration of the AhR agonist from a composition as contemplated and described herein upregulates CYP1A1. FIG. 2B shows that topical administration of the AhR agonist from a composition as contemplated and described herein downregulates the pro-inflammatory cytokine IL17-alpha. FIGS. 2C-2E shows that topical administration of the AhR agonist from a composition as contemplated and described herein downregulates the pro-inflammatory cytokines or antimicrobial peptide, respectively, IL-1beta and IL-8 and S100A7. Accordingly, in embodiments, a composition that downregulates one or more pro-inflammatory cytokines 8, 12, 16, 24 or 40 hours after topical application to skin is contemplated.

Accordingly, in one embodiment, a composition containing an AhR agonist when applied topically to skin achieves upregulation of CYP1A1 in the skin more than 100-fold relative to the same composition lacking the AhR agonist. In another embodiment, a composition containing an AhR agonist when applied topically to skin achieves AhR translocation into the nucleus at a distance of greater than 500, 750 or 1000 μM from the stratum corneum, as measured, for example, by immunohistochemistry. In another embodiment, a composition containing an AhR agonist when applied topically to skin achieves upregulation of CYP1A1 in the skin at a distance of greater than 500, 750 or 1000 μM from the stratum corneum, as measured, for example, by immunohistochemistry or via qPCR. In another embodiment, the upregulation in CYP1A1 and/or translocation of AhR into the nucleus occurs within the sebaceous glands and/or the pilosebacious unit.

Accordingly, in view of the data herein, the composition comprising synthetic indirubin when topically applied to human skin at 10 mg/cm$^2$ provides one or more of the following features: (i) a non-therapeutic systemic blood level of indirubin; (ii) more than about 10 ng per cm$^2$, 12 ng per cm$^2$, 14 ng per cm$^2$, 14.5 ng per cm$^2$, or 14.7 ng per cm$^2$ of indirubin into the epidermis when applied to the skin for 24 hours; (iii) more than about 10 ng per cm$^2$, 12 ng per cm$^2$, 14 ng per cm$^2$, 16.0 ng per cm$^2$, 16.5 ng per cm$^2$, or 16.9 ng per cm$^2$ of indirubin into the dermis when applied to the skin for 24 hours; and (iv) upregulation of CYP1A1 in the skin more than 50-fold, 75-fold, 100-fold or 125-fold relative to the same composition lacking synthetic indirubin. The feature(s) achieved can be on human skin in vitro, or can be human skin in vivo. The skin can be intact or disrupted.

The compositions may be packaged for use in a medical setting or for retail distribution directly to the consumer (i.e., an article of manufacture or kit). Such articles will be labeled and packaged in a manner advising the patient how to use the product for therapy. Such instructions will include the duration of treatment, dosing schedule, precautions, etc. These instructions may be in the form of pictures, written instructions, or a combination thereof. They may be printed on the side of the packaging, be an insert, or any other form of communication appropriate for the retail market.

The composition may conveniently be presented in dosage unit form and may be prepared by any of the methods well known in the art of pharmacy. For example, the composition can be placed in an appropriate container, such as a squeeze-tube with a cap for dispensing ointments and creams, or a device for dispensing unit dosages of the formulation, such as a bottle or dropper that dispenses a controlled pre-determined dosage of the composition to a target area. In a preferred embodiment, the target area is on the skin of a human.

The composition may be part of a kit that allows the user to add a pigment into the formulation to make it closer to one's skin tone. The kit may include a cosmetic or make-up for use prior to or after application of the composition to make the composition less visible.

In the compositions described, the AhR agonist is present in an amount for skin conditions, ailments and/or diseases, such as HS. In one embodiment, the compositions comprise a therapeutically effective amount of the AhR agonist. The amount of compound administered will depend upon a variety of factors, including, for example, the severity of the HS in the patient being treated, the mode of administration, the age and weight of the patient, the bioavailability of the particular active compound, etc. Determination of an effective dosage is well within the capabilities of those skilled in the art. A skilled practitioner will be able to determine the optimal dose for a particular individual. Effective dosages may be estimated initially from in vitro assays.

In one embodiment, topical application of the composition yields no measurable systemic blood level of AhR agonist compound(s), for example, 24 hours or 48 hours after topical administration. In one embodiment, no measureable systemic blood level intends a concentration of the AhR agonist compound(s) that is not substantially greater than a control blood sample from a subject not treated with the composition, and/or not a blood level that is not significant therapeutically.

In one embodiment, the carrier is suitable for topical administration. In one embodiment, the carrier is an ointment. In one embodiment, the carrier is an oleaginous compound and a solvent, optionally with a wax.

The compositions described herein are, in one aspect, for treating HS. The composition is applied topically to a local region of the skin where signs and symptoms of HS (or another inflammatory disease to be treated) are evident. In one embodiment, the formulation is administered in a topical formulation directly to effected skin region, without applying it to any substantial amount onto unaffected skin.

The composition is applied to the skin, in various embodiments, at least once daily, or at least two, three or four times daily. In one embodiment, the topical formulation is applied at least once daily for a period of about 4-12 weeks. In other embodiments, the topical formulation is applied between 1-3 times daily for a period between about 4-12 weeks. In other embodiments, the composition is topically applied 1-2, 1-3, 1-4 or 1-5 times daily for a period of between about 1-2 weeks, 1-3 weeks, 1-4 weeks, 1-6 weeks, 1-8 weeks, 1-10 weeks, 1-12 weeks, 1-16 weeks, 1-20 weeks, 1-24 weeks, 1-2 months, 1-3 months, 1-4 months, 1-6 months, 1-8 months, 1-10 months, 1-12 months. The dosing schedule will depend, as can be appreciated, by factors well known in medical arts, including the dose of drug compound in the formulation, the severity of the disorder, and the health of the patient.

B. Exemplary Conditions for Treatment

As can be appreciated based on the foregoing, compositions comprising an AhR agonist are contemplated. The compositions are suitable for treating conditions responsive to activation of the AhR. The compositions are preferably topical compositions for application to skin affected by a skin disorder, for treatment of the skin disorder. In one embodiment, the topical composition downregulates one or more pro-inflammatory cytokines to treat, alleviate symptoms of, or prevent recurrence of symptoms or a disorder.

Disorders or conditions contemplated for treatment with the compositions include, in certain embodiments, hidradenitis suppurativa (HS), pyoderma gangrenosum (PG), psoriasis (Ps), atopic dermatitis (AD), palmoplantar pustulosis (PPP), and/or prurigo nodularis (PN).

In a first aspect, methods for treating HS, PG, Ps, AD, PPP and PN are contemplated. The methods comprise administering to a subject a therapeutically effective amount of a composition comprising an aryl hydrocarbon receptor agonist or modulating agent, thereby treating or preventing HS, PG, psoriasis and/or atopic dermatitis in the subject. In another aspect, a method for alleviating symptoms associated with HS, PG, Ps, AD, PPP and/or PN comprises administering to a subject a therapeutically effective amount of a composition comprising an aryl hydrocarbon receptor agonist or modulating agent, thereby alleviating symptoms associated with HS, PG, Ps, AD, PPP and/or PN in the subject.

In still another aspect, a method for treating HS, PG, Ps, AD, PPP and/or PN in a subject previously treated for HS, PG, Ps, AD, PPP and/or PN by administration of an active agent other than an aryl hydrocarbon receptor agonist, such as, for example, an antibiotic, a retinoid, a Janus kinase inhibitor, a PDE-4 inhibitor, a complement inhibitor, an anti-TNF-alpha antibody, an anti-IL-17 antibody, an anti-IL-23 antibody, anti-androgens and/or a steroid. The method comprises administering to the subject a therapeutically effective amount of a composition comprising an aryl hydrocarbon receptor agonist or modulating agent, thereby treating HS, PG, Ps, AD, PPP and/or PN in the refractory subject.

In another aspect, a method for preventing recurrence of symptoms associated with HS, PG, Ps, AD, PPP and/or PN or for reducing frequency of HS, PG, Ps, AD, PPP and/or PN in a subject diagnosed with HS, PG, Ps, AD, PPP and/or PN is provided. The methods comprise administering to the subject a therapeutically effective amount of a composition comprising an aryl hydrocarbon receptor agonist or modulating agent, thereby preventing recurrence of symptoms or reducing frequency of HS, PG, Ps, AD, PPP and/or PN in the subject.

Pyoderma gangrenosum, or PG, as mentioned herein is a typical ulcerative form, which often occurs on the legs, and/or the atypical form that is more superficial and often occurs on other parts of the body. The term also encompasses, unless otherwise specified, peristomal pyodermal gangrenosum, pustular pyodermal gangrenosum or vegetative pyodermal gangrenosum. Forms of PG that are idiopathic or of known cause are included, as are forms of PG that appear at the site of trauma including surgical wounds.

Aopic dermatitis, or AD, is also referred to as eczema. It can be diffuse or limited to a specific part of the body. It can occur in infants, children and adults. There are several different types of eczema including contact dermatitis, dyshidrotic eczema, nummular eczema, seborrheic dermatitis and stasis dermatitis. In an embodiment, the condition to be treated by topical application of a composition as described herein is AD. Atopic dermatitis is a common skin disease that often first occurs in children characterized red itchy, sometimes flaky skin and is thought to be a form an allergic or Th2 type immune response. There are certain diseases that may be distinct in pathophysiology but which as considered forms of atopic dermatitis. These include seborrheic dermatitis and hand eczema.

Prurigo nodularis, or PN, is a skin disease that causes hard, itchy lumps (nodules) to form on the skin. The itching (pruritus) can be intense, causing afflicted persons to scratch to the point of bleeding or pain. The intensely itchy skin may interfere with sleep or with everyday activities. The nodules can range in size from very small to about half an inch in diameter. The nodules often have a rough, dry top and can range in number from a few to hundreds. Nodules most commonly form on the outer arms, shoulders, and legs, but may also occur on the neck and trunk, and they rarely form on the face and palms. They may be lighter or darker in color than the surrounding skin. Scarring may occur after nodules begin to heal. The symptoms of PN can begin at any age but are most common in adults between 20-60 years. In an embodiment, the condition to be treated by topical application of a composition as described herein is PN.

Palmoplantar pustulosis, or PPP, is a skin condition that presents mainly on the palms and soles of the feet. PPP is sometimes also referred to as pustular psoriasis of the palms and soles because some affected persons also have psoriasis. It sometimes runs in families and rarely occurs before adulthood. The skin develops tiny fluid filled blisters that fill with a small amount of pus, turn brown, then scaly. The scaling may be so prominent that only redness and scaling is seen. They come in waves or crops on one or both hands and/or feet and cause thickened, scaly, red skin that easily develops painful cracks (fissures). The condition varies in severity and may persist for many years. In an embodiment the condition to be treated is PNN.

In an embodiment, the condition to be treated is HS. HS is a chronic, inflammatory, recurrent, debilitating skin disease, which typically presents after puberty with painful, inflamed lesions in apocrine gland bearing areas of the body. Severity of HS is classified by various measures, such as Hurley classification, the Modified Sartorius Score, and the International Hidradenitis Suppurativa Severity Score System (Zouboulis, C. C. et al., British Journal of Dermatology, 177(5)L1401 (2017)). The Hurley staging system is commonly used, and divides HS into three stages—Stage I, characterized by single or multiple abscesses without sinus tract formation or scarring; Stage II, characterized by recurrent abscesses with one or more sinus tracts and scarring widely separated by normal skin; and Stage III, characterized by diffuse involvement with multiple sinus tracts and no intervening normal skin (Hurley H. J., In: Roenigk R K, Roenigk H H Jr, eds. Roenigk and Roenigk's Dermatologic Surgery: Principles and Practice. 2nd ed. New York, N.Y.: Marcel Dekker; 1996:623-645). The methods described herein contemplate treatment of subjects with Hurley stage I HS, Hurley stage II HS, and/or Hurley stage III HS.

Examples 7-9 describe treatment of subjects with HS. In one embodiment, the composition with an AhR receptor agonist is applied twice daily to the affected area. A marked improvement is observed within 7 days, with a continued diminishment of symptoms over the month long study period. In another embodiment, the composition with an AhR receptor agonist is applied once daily for 8 weeks. A reduction in the number of new inflammatory nodules is observed. A resolution of inflammatory nodules, abscesses and fistulas in observed compared to a placebo formulation. The reduction results in a 50% or greater reduction on the HiScore grading of HS. In another embodiment, the composition with an AhR receptor agonist is applied once daily for 8 weeks. A reduction in the number of new inflammatory nodules is observed. A resolution of inflammatory nodules, abscesses and fistulas in observed compared to a placebo formulation. The reduction results in a 50% or greater reduction on the HiScore grading of HS.

In an embodiment, the condition to be treated is pyoderma gangrenosum (PG). PG is a rare chronic inflammatory skin disease defined by painful nodules or pustules that become ulcers and progressively grow. The cause is unknown, but is characterized by lesions with extensive immune infiltrates. PG is often misdiagnosed and improperly treated with antibiotics. PG lesions may come and go or linger for extended periods of time. The lesions often result in open wounds that do not heal for an extended period. Often times, trauma results in the development of new lesions. In an embodiment, the condition to be treated by topical application of a composition as described herein is PN.

In another embodiment, the conditions to be treated are neutrophilic dermatoses that may manifest in skin ulcers. These diseases may include HS and PG and acne but also rare diseases such as PAPA, PASH and PAPASH syndromes linked to mutation in the PSTPIP-1 gene. All of these diseases are defined by skin regions of sterile or non-sterile neutrophil rich inflammation.

Psoriasis, or Ps, is a common chronic inflammatory skin disease defined by red, sometimes itchy, scaly patches on the skin. The condition includes plaque psoriasis, guttate psoriasis, inverse psoriasis, pustular psoriasis (whether on the palms or other locations) or erthrodermic psoriasis. It also includes psoriasis localized to a particular anatomic region such as the scalp, the hands, the feet, under the arm or in the groin, the elbows, the knees, the lower back, under the nails or the nail bed and to psoriatic arthritis. Accordingly, in another embodiment, the condition to be treated is Ps. Severity may be established by the percentage of the body surface area (BSA) covered with lesions or via the psoriasis area and severity index (PASI) or the physician global assessment (PGA) although many other assessment tools have also been used. There are many approved FDA therapies for treating psoriasis, but they are often inconvenient, ineffective, expensive, or lead to the development of adverse events. There are certain psoriatic diseases that may be distinct in pathophysiology but which as considered forms of psoriasis. These include palmoplantar pustulosis, scalp psoriasis, and nail psoriasis. In an embodiment, the condition to be treated by topical application of a composition as described herein is Ps.

In another embodiment the condition to be treated is pruritic or itchy skin. Many diseases many cause pruritus including generalized pruritus, purigo nodularis, psoriasis and eczema. The treatment many either treat just the pruritus or the underlying condition. Purigo nodularis is a skin disease characterized by hard itchy lumps on the skin. The cause of the disease is not known and it is exacerbated by scratching.

The compositions are also contemplated for use in alleviating symptoms associated with HS in the subject and/or preventing recurrence of HS. The compositions are also contemplated for treating HS in a subject previously treated for HS with an active agent other than an AhR agonist. In one embodiment, the subject with HS was refractory to treatment with the agent that was not an AhR agonist. In other embodiments, the subject with HS was refractory to treatment with, for example, antibiotics, anti-androgens (e.g. spironolactone), retinoids, Janus-kinase (JAK) inhibitors, complement inhibitors (e.g., complement component 5a), an anti-TNF-alpha antibody (e.g., infliximab, adalimumab), a Th17 type cytokine or chemokine blocking antibody such as IL-17, IL-8, or IL-23 (e.g., secukinumab, bimikizumab, guselkumab, ustekinumab), IL-1 (eg. bermekimab), a phosphodiesterase-4 inhibitor (eg. crisaborole, apremilast, roflumilast) and/or a steroid.

The methods and compositions can optionally be used in combination with one or more other therapies, such as one or more therapeutic agents, surgery and/or radiation. Therapeutic agents include antibiotics (oral or topical), antiseptic agents, and the like. In other embodiments, the methods and compositions provided herein are used in combination with one or more therapeutic agents.

Compositions comprising an AhR agonist, such as those described herein, are also contemplated for use in treating other skin diseases such as acne, acne inversa, acral fibrokeratoma, acrodermatitus enterpathica, acrokeratoelastoidosis, actinic keratosis (solar keratoses), adenoma sebaceum, angiokeratoma, atopic dermatitis, basal cell carcinoma, Bechet's disease, benign fibrous histiocytomas, bladder cancer, Bowen's disease, breast cancer, Buschke-Ollendorff syndrome, bullous pemphigold, cervical cancer, cervical dysplasia, cherry angiomas, chondrodermatitis nodularis chronica helicis, contact dermatitis, cutaneous Crohn's disease, cutaneous endometriosis, cutaneous leukemia, cutaneous lymphoma, cutaneous meningioma, cutaneous myxoma, Darier's disease, dermal dendrocyte hamartoma, dermatofibroma, dermatofibrosarcoma protuberans, eccrine angiomatous hamartoma, ectodermal dysplasia, epidermal inclusion cysts, epidermal naevi (including but not limited to nacvus scbaccous, comedone nacvus, Proteus syndrome, becker naevous), epithclioid cell histiocytoma, erythoderma, familial myxovascular fibromas, fungal skin disease (including lobomycosis), granular cell tumor, glucaonoma syndrome, genital warts, Hailey-hailey disease, ichthyosis (including but not limited to ichthyosis vulgaris, ichthyosis lamellaria, X-linked ichthyosis, epidermolytic hyperkeratosis, ichthyosis acquista and keratosis palmoplantaris), idiopathic guttate hypomelanosis, impetigo, infantile acropustulosis, infantile fibromatosis, Kaposi's sarcoma, keloid, keratoacanthoma, keratocyst, knuckle pads, lice, lentigo, melanoma, microvenular hemangioma, Morton's neuroma, mucus membrane pemphigold, multifocal lymphangioendotheliomatosis, multinucleate cell angiohistocytoma, multiple cutaneous leciomyomas, mumps, mycosis fungoides, nail psoriasis, Netherton syndrome, neuroma cutis, neurothekeoma, nevus flammeus, nevus lipomatosus superficialis, pachydermodactyly, palisaded encapsulated neuroma, parasitic skin diseases (including but not limited to scabies, pediculosis, tungiasis, hookwork-related cutaneous larva migrans), pityriasis ruba pilaris, piloleiomyomas, plexiform fibrohistiocytic tumor, porokeratotic eccrine ostial and dermal duct nevus, progressive nodular histiocytoma psoriasis (including but not limited to psoriatic erytroderma, palmoplantar psoriasis, palmoplantar pustolosis, generalized pustular psoriasis of Zumbusch, lingua geographical), PAPA syndrome, PAPSH syndrome, PASH syndrome, pemphis vulgaris, pityriasis lichenoides chronica, porokeratosis, proctitis, purigo nodularis, pyoderma gangrenosum, seborrhoeic dermatitis, seborrhoeic keratosis, rhinophyma, rosacea, solitary cutaneous leiomyoma, Sjögren syndrome, spider angioma, targetoid hemosiderotic hemangioma, squamous cell carcinoma, Sweet's syndrome, systemic lupus erythematosus, tufted angioma, venous lake, vitiligo, urticaria pigmentosa, xanthelasmoidal mastocytosis or zosteriform metastasis.

Other skin ailments can also be treated with an AhR agonist including, without limitation, anaphylactoid purpura, arthritis-associated rash, benign epidermal cysts, birthmarks, calluses, corns, eczema, freckles, dyschromatosis symmetrica hereditaria, dyschromatosis universalis hereditaria, diabetic foot ulcers, familial progressive hyperpigmentation, Galli Galli disease, hemosiderin hyperpigmentation, idiopathic guttate hypomelanosis, iron metallic discoloration, leukoderma, lupus-associated rash, melasma, moles, Mukamel syndrome, necklace of Venus, nevus anemicus, nevus depigmentosus, Pallister-Killian syndrome, phylloid hypomelanosis, piebaldism, pigmentatio reticularis facici et colli, pigmentation disorders (drug induced hyperpigmentation), pilar cysts, pityriasis alba, pityriasis rosea, poikiloderma of civatte, poikiloderma vascular atrophicans, postinflammatory hyperpigmentation, progressive macular hypomelanosis, pruritus, reticular pigmented anomaly of the flexures, reticulate acropigmentation of Kitamura, Riehl melanosis, Shah-Waardenburg syndrome, shitake mushroom dermatitis, tar melanosis, titanium metallic discoloration, transient neonatal pustular melanosis, Vagabond's leukomelanoderma, vasospastic macules, Wende-Bauckus syndrome, X-linked reticulate pigmentary disorder, Yemenite deaf-blind hypopigmentation syndrome, scars, skin tags, tattoo removal or vitiligo (including but not limited to non-segmented vitiligo).

III. Examples

The following examples are illustrative in nature and are in no way intended to be limiting.

Example 1

Exemplary Compositions

Compositions comprised of indigo are prepared as topical formulations with the ingredients and amounts (in weight percent based on total weight of the formulation) as shown in Table 1-1.

TABLE 1-1

| Ingredients | wt/wt % | wt/wt % | wt/wt % | wt/wt % | wt/wt % | wt/wt % | wt/wt % | wt/wt % | wt/wt % |
|---|---|---|---|---|---|---|---|---|---|
| indigo | 7 | 7 | 7 | 7 | 7 | 7 | 7 | 7 | 7 |
| dimethyl sulfoxide | 93 | | | | | | | | |
| di-propylene glycol | | 93 | | | | | | | |
| ethanol | | | 93 | | | | | | |
| isopropanol | | | | 93 | | | | | |
| PEG 300 | | | | | 93 | | | | |
| propylene glycol | | | | | | 93 | | | |
| diethylene glycol monoethyl ether (Transcutol ®) | | | | | | | 93 | | |
| PEG 400 | | | | | | | | 93 | |
| water | | | | | | | | | 93 |

Example 2

In Vitro Penetration and Pharmacokinetics in Human Skin of Topical Compositions Comprising Synthetic Indirubin Compositions comprised of synthetic indirubin were prepared as topical formulations with the ingredients in the amounts (in weight percent based on total weight of the formulation) shown in Tables 2-1, 2-2 and 2-3.

The formulations were prepared by first adding synthetic indirubin and any antioxidant(s) into the non-oleaginous solvent(s) to either dissolve or suspend the synthetic indirubin in the solvent(s). Then, the oleaginouos component (oily liquid or polyethylene glycol component) and the wax component were added to the dissolved/suspended indirubin-solvent mixture. The oleaginouos component was heated to about 75° C. before addition. The mixture was homogenized for 2 minutes using a Silverson L4RT homogenizer at 10,000 RPM and then stirred on an IKA hotplate at 550 RPM until cooled to ambient temperature. The formulation identified as Formulation No. 438S was prepared as described in this Example; the formulation identified as Formulation No. 438N was prepared as described in U.S. Pat. No. 9,833,438, incorporated by reference herein.

TABLE 2-1

| | Formulation Identification No. | | | | | | | | |
|---|---|---|---|---|---|---|---|---|---|
| Ingredient | OO02 | OO09 (0.08%) | OO09 (0.20%) | OO14 | OO17 | OO19 | PO01 | PO03 | 438N 438S |
| Indirubin | 0.025 | 0.08 | 0.20 | 0.08 | 0.20 | 0.20 | 0.11 | 0.11 | 0.02 |
| Olive oil | 65.7 | 63.1 | 63.0 | — | 66.3 | — | — | — | 83.3 |
| Castor oil | — | — | — | 53.1 | — | 62.2 | — | — | — |

TABLE 2-1-continued

| Ingredient | OO02 | OO09 (0.08%) | OO09 (0.20%) | OO14 | OO17 | OO19 | PO01 | PO03 | 438N 438S |
|---|---|---|---|---|---|---|---|---|---|
| diethylene glycol monoethyl ether (TRANSCUTOL ® HP) | 8.8 | — | — | — | — | 16.7 | 15.0 | — | — |
| Propylene glycol | — | — | — | — | 16.7 | — | — | — | — |
| Isopropyl myristate | 0.83 | — | — | — | — | 4.2 | — | — | — |
| DMSO* | — | 20.0 | 20.0 | 30.0 | — | — | 15.0 | 20.0 | — |
| NMP* | 8.33 | — | — | — | — | — | — | — | — |
| Super Refined PEG* 4000 | — | — | — | — | — | — | 49.8 | 59.8 | — |
| PEG* 4000 | — | — | — | — | — | — | 20.0 | 20.0 | — |
| Beeswax | 16.7 | 16.7 | 16.7 | 16.7 | 16.7 | 16.7 | — | — | 16.7 |
| Butylated hydroxytoluene | 0.1 | 0.1 | 0.1 | 0.1 | 0.1 | 0.1 | 0.1 | 0.1 | — |

*DMSO = dimethylsulfoxide;
NMP = n-methyl-2-pyrrolidone
PEG = polyethylene glycol

TABLE 2-2

| Ingredient | OO29 | OO75 | OO76 | OO40 | OO54 |
|---|---|---|---|---|---|
| Indirubin | 0.02 | 0.02 | 0.02 | 0.02 | 0.02 |
| Castor oil | — | — | — | 53.2 | — |
| Mineral oil | — | 25.0 | — | — | — |
| Oleic acid | 25.0 | 25.0 | — | — | — |
| Diethyl sebacate | — | — | — | — | 24.0 |
| TRANSCUTOL ® P | 15.0 | 15.0 | 15.0 | 11.0 | 15.0 |
| DMSO* | — | — | 5.0 | 10.0 | 10.0 |
| NMP* | 5.0 | 5.00 | 5.0 | — | — |
| Isopropyl myristate | 5.0 | 5.00 | — | 9.0 | 9.0 |
| Butylated hydroxytoluene | 0.1 | 0.10 | 0.1 | 0.1 | 0.1 |
| POLAWAX ™ NF | 15.0 | 15.00 | 15.0 | — | — |
| Poloxamer 407 | — | — | — | — | 15.0 |
| White soft paraffin | 34.9 | 34.9 | 34.9 | — | 26.9 |
| Beeswax | — | — | — | 16.7 | — |

*DMSO = dimethylsulfoxide;
NMP = n-methyl-2-pyrrolidone

TABLE 2-3

| Ingredient | OO61 | OO77 | OO65 | OO66 | OO67 | OO73 |
|---|---|---|---|---|---|---|
| Indirubin | 0.014 | 0.016 | 0.010 | 0.012 | 0.036 | 0.10 |
| Mineral oil | — | — | 20.0 | 20.0 | 20.0 | 9.1 |
| Oleic acid | 10.0 | 10.0 | — | — | — | — |
| TRANSCUTOL ® P | 15.0 | 15.0 | 10.0 | 10.0 | — | 30.0 |
| DMSO* | — | 10.0 | 10.0 | 10.0 | — | 25.0 |
| NMP* | 10.0 | — | — | — | 15.0 | — |
| Propylene glycol | — | — | — | 2.5 | — | — |
| Glycerol | — | — | 2.5 | — | 2.5 | — |
| Isopropyl myristate | 2.5 | 2.5 | — | — | — | 5.0 |
| BHT* | 0.1 | 0.1 | 0.1 | 0.1 | 0.1 | 0.1 |
| SEPINEO ™ P600 | — | — | 4.0 | 4.0 | 4.0 | — |
| Poloxamer 407 | 10.0 | 10.0 | — | — | — | 9.1 |
| Aluminum starch octenylsuccinate | 5.0 | 5.0 | — | — | — | — |
| White soft paraffin | 32.4 | 32.4 | 41.4 | 41.4 | 46.4 | 15.7 |
| Cetostearyl alcohol (KOLLIWAX ® CSA 50) | — | — | 12.0 | 12.0 | 12.0 | 6.0 |
| Cetyl alcohol (KOLLIWAX ® CA) | 7.5 | 7.5 | — | — | — | — |
| MEDILAN ™ Ultra (Lanolin) | 7.5 | 7.5 | — | — | — | — |

*DMSO = dimethylsulfoxide;
NMP = n-methyl-2-pyrrolidone
BHT = butylated hydroxytoluene Each formulation was tested for in vitro skin penetration using human cadaver skin. The skin was dermatomed to 500 microns in thickness with the stratum corneum intact and placed on the in vitro diffusion apparatus with the stratum corneum side facing the donor well. 10 mg of each formulation was applied to the 1 cm² skin surface area to provide a dose of 10 mg/cm². The receptor solution of citrate/phosphate buffer pH 5.6 with 0.01% BRIJ 98 was continuously flowed under the skin mounted in the apparatus at 8 μL/minute. After 24 hours, residual formulation was removed from the skin with a KIMWIPE™. The stratum corneum was removed from the skin via tape-stripping with D-SQUAME® tape. The epidermis and dermis were separated after heating at 60° C. for 2 minutes and then homogenized and extracted using 90:10 acetonitrile/water. The amount of the AhR agonist indirubin in each of the epidermis, dermis and receptor solution was determined via LC-MS/MS. The receptor solution was automatically collected every two hours for testing. As comparative controls, an ointment of *Indigo naturalis* plant extract was prepared (as described as in patent U.S. Pat. No. 9,833,438, the method of preparation incorporated by reference herein) and is identified herein as Formulation Identification No. 438N when made from *Indigo naturalis* and as Formulation Identification No. 438S when made with synthetic indirubin.

Results are shown in Tables 1A-1C, above, and in FIGS. 1A-1B.

Example 3

In Vitro Penetration and Pharmacokinetics in Human Skin of Topical Compositions Comprising Synthetic Indirubin The compositions identified as formulation nos. OO29, OO75, OO76, OO40, OO54, OO61, OO77, OO65, OO67 and OO73 are tested as described in Example 2 and compared to the formulation no. 438N. The formulations (with the exception of 438N) contained synthetic indirubin that is fully in solution and is both chemically and physically stable over 2, 4, 6 or 12 months at 25° C. The test formulations deliver significantly more indirubin in the dermis, epidermis and receiver solution at 24 hours than the comparative control formulation no. 438N even though the test formulations contain less than or equivalent levels of indirubin. It is found that the test formulations deliver more than about 14.7 ng per cm$^2$ of indirubin (6.4 µM) into the epidermis and more than about 16.9 ng per cm$^2$ of indirubin (0.7 µM) into the dermis after 24 hours. The flux of all formulations is significantly greater than 0.1 ng/cm$^2$/hr though the treated skin resulting in a cumulative amount of indirubin in the receptor solution of greater than 1.10 ng/cm$^2$ after 24 hours.

Example 4

Exemplary Compositions

Compositions comprised of tapinarof are prepared as topical formulations following the procedure, for example, of Example 2. The formulations have the components specified in Tables 4-1 and 4-2.

TABLE 4-1

| Ingredients | wt/wt % | wt/wt % | wt/wt % | wt/wt % | wt/wt % | wt/wt % | wt/wt % | wt/wt % | wt/wt % |
|---|---|---|---|---|---|---|---|---|---|
| tapinarof | 10 | 10 | 10 | 10 | 10 | 10 | 10 | 10 | 10 |
| dimethyl sulfoxide | 90 | | | | | | | | |
| di-propylene glycol | | 90 | | | | | | | |
| ethanol | | | 90 | | | | | | |
| isopropanol | | | | 90 | | | | | |
| PEG 300 | | | | | 90 | | | | |
| propylene glycol | | | | | | 90 | | | |
| diethylene glycol monoethyl ether (TRANSCUTOL ®) | | | | | | | 90 | 90 | |
| water | | | | | | | | | 90 |

TABLE 4-2

| Ingredients | TP01 | TP02 | TP03 | TP04 | TP05 | TP06 |
|---|---|---|---|---|---|---|
| Tapinarof | 1.014 | 1.016 | 1.01 | 1.012 | 1.036 | 1.10 |
| Mineral oil | | | 20.00 | 20.00 | 20.00 | 9.08 |
| Oleic acid | 10.00 | 10.00 | | | | |
| TRANSCUTOL ® P | 15.00 | 15.00 | 10.00 | 10.00 | | 30.00 |
| DMSO* | — | 10.00 | 10.00 | 10.00 | | 25.00 |
| NMP* | 10.00 | | | | 15.00 | |
| Propylene glycol | | | | 2.50 | | |
| Glycerol | | | 2.50 | | 2.50 | |
| Isopropyl myristate | 2.50 | 2.50 | | | | 5.00 |
| BHT* | 0.10 | 0.10 | 0.10 | 0.10 | 0.10 | 0.10 |
| SEPINEO ™ P600 | | | 4.00 | 4.00 | 4.000 | |
| Poloxamer 407 | 10.00 | 10.00 | | | | 9.08 |
| Aluminium starch octenylsuccinate | 5.00 | 5.00 | | | | |
| White soft paraffin | 31.39 | 31.38 | 13.39 | 40.39 | 45.36 | 14.68 |
| Cetostearyl alcohol (KOLLIWAX ® CSA 50) | — | — | 12.00 | 12.00 | 12.00 | 5.96 |
| Cetyl alcohol (KOLLIWAX ® CA) | 7.50 | 7.50 | — | — | — | — |
| MEDILAN ™ Ultra (Lanolin) | 7.50 | 7.50 | — | — | — | — |

*DMSO = dimethylsulfoxide;

NMP = n-methyl-2-pyrrolidone;

BHT = butylated hydroxytoluene

The compositions in the above tables are used to treat any of the conditions described herein, including psoriasis (Ps), atopic dermatitis (AD), contact dermatitis, hidradenitis suppurativa (HS), pyoderma gangrenosum (PG), Sweet's syndrome, mutations in the PSTPIP-1 gene (PAPA syndrome, PAPSH syndrome and PASH syndrome), Bechet's disease, bullous pemphigold, mucous membrane pemphigold, pemphis vulgaris, cutaneous Crohn's disease, Sjögren syndrome, systemic lupus erythematosus, prurigo nodularis (PN), pityriasis lichenoides chronica, palmoplantar pustulosis (PPP), and erythroderma. The compositions are tested in in vitro skin penetration assays using human cadaver skin as described in Example 2. The compositions are tested for stability using a stability assay. The compositions are used in in vitro pharmacodynamic assays skin as described in Example 4.

Example 5

Pharmacodynamics

Freshly excised human skin was dermatomed to 750 microns with the stratum corneum intact and placed on a static Franz cell employing ~0.6 cm² of skin. 10 µL of a topical formulation OO14 containing 0.079% synthetic indirubin was applied to the skin at either 16 hours prior to stimulation or both 40 hours and 16 hours prior to Th17 stimulation. As a control, 0.01% betamethasone (BMV) was added to the receptor solution at both 40 hours and 16 hours prior to Th17 stimulation. The Th17 stimulation media contains a mixture of cytokines and antibodies shown to induce Th17 polarization and was made and added as described in the skin resident immune cell activation assay in Smith S. H. et al., PLoS ONE 11(2): e0147979. The skin was cultured for an additional 24 hours prior to harvesting for qPCR and staining for AhR activation. CYP1A1 was chosen as it is a readout for AhR activation as it is poorly expressed under normal conditions and upregulated by activated AhR. IL-17a, IL-1B, S100A7 and IL-8 were chosen as they are mediators associated with Th-17 type inflammation and have been shown to be significantly upregulated in HS lesions (Frew et al., F1000 Research 2018, 7:1930). Results are shown in Table 2 and in FIGS. 2A-2E.

Example 6

Pharmacodynamics

The compositions identified as formulation nos. OO29, OO75, OO76, OO40, OO54, OO61, OO77, OO65, OO67, OO73 and their matched placebos are tested in a pharmacodynamic (PD) study as described in Example 5, with an increased number of skin donors and with additional qPCR analytes. The epidermal and dermal PD is determined after a single 10 µL application of the formulation to the skin 16 hours prior to Th17 polarization. Additional qPCR analytes include IL-22, CCL20, TNFα and S100A9. There is a significant increase in CYP1A1 and IL-22 noted in the treated samples compared to matched placebo controls. There is a significant reduction in IL-17α, IL-1β, S100A1, S100A9, IL-8, CCL20 and TNFα.

Formulation nos. OO29, OO75, OO76, OO40, OO54, OO61, OO77, OO65, OO67, OO73 and their matched placebos are tested in lesional living skin biopsies from HS patients. This skin is split into two equal portions and placed on a Franz cell as described above in Example 2 and treated with 10 µL of each formulation or a matched placebo. After 24 hours, the skin is harvested for qPCR analysis. There is a significant increase in CYP1A1 and IL-22 noted in the treated samples compared to matched placebo controls. There is a significant reduction in IL-17α, IL-1β, S100A1, S100A9, IL-8, CCL20 and TNFα.

Formulation nos. OO29, OO75, OO76, OO40, OO54, OO61, OO77, OO65, OO67, OO73 and their matched placebos are tested on distinct active HS lesions. 0.5 g of each formation or placebo is applied to a 10 cm diameter area containing an active lesion twice daily for 7 days. After 7 days, a skin biopsy is harvested for qPCR analysis. There is a significant increase in CYP1A1 and IL-22 noted in the treated samples compared to matched placebo controls. There is a significant reduction in IL-17α, IL-1β, S100A1, S100A9, IL-8, CCL20 and TNFα.

Example 7

Treatment of HS

A composition comprising synthetic indirubin is prepared as described in Example 2 and is topically applied to skin of subjects with HS. The composition is applied twice daily to the affected area. A marked improvement is observed within 7 days, with a continued diminishment of symptoms over the month long study period.

Example 8

Treatment of HS

A composition of Example 2 identified as OO14 is prepared and is topically applied to skin of subjects with HS. The composition is applied once daily for 8 weeks. A reduction in the number of new inflammatory nodules is observed. A resolution of inflammatory nodules, abscesses and fistulas in observed compared to a placebo formulation. The reduction results in a 50% or greater reduction on the HiScore grading of HS.

Example 9

Treatment of HS

A composition comprising tapinarof is prepared as described in Example 4 and is topically applied to skin of subjects with HS. The composition is applied once daily for 8 weeks. A reduction in the number of new inflammatory nodules is observed. A resolution of inflammatory nodules, abscesses and fistulas in observed compared to a placebo formulation. The reduction results in a 50% or greater reduction on the HiScore grading of HS.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:
1. A method for treating hidradenitis suppurativa (HS), comprising:
administering to a subject a therapeutically effective amount of a composition comprising synthetic indirubin, thereby treating HS in the subject.

2. The method of claim 1, wherein the composition further comprises a pharmaceutically acceptable carrier.

3. The method of claim 2, wherein the pharmaceutically acceptable carrier is a wax component selected from beeswax, paraffin wax, and lanolin wax.

4. The method of claim 2, wherein the pharmaceutically acceptable carrier is a compound that is an oily liquid at 23-25° C.

5. The method of claim 4, wherein the oily liquid is oleic acid or diethyl sebacate.

6. The method of claim 2, wherein the composition comprises an aprotic solvent.

7. The method of claim 6, wherein the aprotic solvent is isopropyl myristate or dimethyl sulfoxide.

8. The method of claim 1, wherein administering comprises topically administering the composition to a region on the subject affected by HS.

9. The method of claim 1, wherein the administering is to a subject selected from the group consisting of subjects diagnosed with Hurley stage I HS, Hurley stage II HS or Hurley stage III HS.

10. The method of claim 8, wherein the composition comprises between about 0.001-0.5 wt % synthetic indirubin.

11. The method of claim 10, wherein the composition comprises a solvent in which the synthetic indirubin is in solution.

12. The method of claim 11, wherein the solvent is a mixture of two or more solvents that comprises an aprotic solvent.

13. The method of claim 12, wherein the aprotic solvent is a solvent selected from the group consisting of an amide, an ester of an acid, an ester of an alcohol, an ether, a ketone, a lactone and a sulfoxide.

14. The method of claim 13, wherein the aprotic solvent is selected from the group consisting of an amide, a carboxylic acid esters, fatty acid esters, and a sulfoxide.

15. The method of claim 13, wherein the aprotic solvent is selected from the group consisting of isopropyl myristate, ethyl oleate, methyl lactate, dimethyl sulfoxide and decylmethylsulfoxide.

16. The method of claim 12, wherein the mixture comprises a solvent selected from the group consisting of diethylene glycol monoethyl ether, oleic acid, n-methyl-2-pyrrolidone and dimethyl sulfoxide.

17. The method of claim 12, further comprising a wax component.

18. The method of claim 17, wherein the composition comprises between about 15-60 wt % of the wax component.

* * * * *